(12) United States Patent
Lin et al.

(10) Patent No.: US 10,578,889 B2
(45) Date of Patent: Mar. 3, 2020

(54) CONTACT LENS PRODUCT

(71) Applicant: LARGAN MEDICAL CO., LTD., Taichung (TW)

(72) Inventors: En-Ping Lin, Taichung (TW); Wei-Yuan Chen, Taichung (TW); Chun-Hung Teng, Taichung (TW)

(73) Assignee: LARGAN MEDICAL CO., LTD., Taichung (TW)

( * ) Notice: Subject to any disclaimer, the term of this patent is extended or adjusted under 35 U.S.C. 154(b) by 0 days.

(21) Appl. No.: 16/452,725

(22) Filed: Jun. 26, 2019

(65) Prior Publication Data

US 2019/0317339 A1    Oct. 17, 2019

Related U.S. Application Data

(63) Continuation of application No. 15/401,142, filed on Jan. 9, 2017, now Pat. No. 10,371,966.

(30) Foreign Application Priority Data

Feb. 4, 2016    (TW) .............................. 105103797 A

(51) Int. Cl.
*G02C 7/10* (2006.01)
*A61K 9/00* (2006.01)
(Continued)

(52) U.S. Cl.
CPC ............. *G02C 7/104* (2013.01); *A61K 9/0051* (2013.01); *A61K 9/06* (2013.01); *A61K 38/168* (2013.01);
(Continued)

(58) Field of Classification Search
CPC .......... G02C 7/02; G02C 7/028; G02C 7/101; G02C 7/04; G02C 7/061; G02C 7/083; G02C 2202/20; G02C 2202/18; G02C 7/027; G02C 2202/16; G02C 2202/22; G02C 7/12; G02C 7/022; G02C 7/024; G02C 7/044; G02C 7/102; G02C 7/041; G02C 7/06; G02C 13/005; G02C 1/02; G02C 7/042; G02C 7/068; G02C 7/088; G02C 13/001; G02C 13/003; G02C 1/023; G02C 1/10; G02C 2202/10; G02C 2202/24; G02C 5/00; G02C 7/025; G02C 7/047; G02C 7/049; G02C 7/063; G02C 7/066; G02C 7/085; G02C 7/086; G02C 7/10; G02C 7/104; G02C 7/105; G02C 11/02; G02C 11/12; G02C 1/00; G02C 1/04;
(Continued)

(56) References Cited

U.S. PATENT DOCUMENTS 8,153,703 B2    4/2012 Laredo
8,262,947 B2    9/2012 Laredo
(Continued)

FOREIGN PATENT DOCUMENTS

CN    102203072 A    9/2011
CN    102382237 A    3/2012
(Continued)

*Primary Examiner* — Collin X Beatty
*Assistant Examiner* — Grant A Gagnon
(74) *Attorney, Agent, or Firm* — McClure, Qualey & Rodack, LLP

(57) ABSTRACT

A contact lens product includes a contact lens and a buffer solution. The contact lens is immersed in the buffer solution, and the buffer solution includes a cycloplegic agent.

17 Claims, 21 Drawing Sheets

(51) Int. Cl.
| | | |
|---|---|---|
| A61K 47/34 | (2017.01) | |
| A61K 9/06 | (2006.01) | |
| A61K 47/32 | (2006.01) | |
| A61K 38/16 | (2006.01) | |
| A61K 47/22 | (2006.01) | |
| G02B 1/04 | (2006.01) | |
| G02C 7/04 | (2006.01) | |
| A61K 47/14 | (2017.01) | |

(52) U.S. Cl.
CPC .............. *A61K 47/14* (2013.01); *A61K 47/22* (2013.01); *A61K 47/32* (2013.01); *A61K 47/34* (2013.01); *G02B 1/043* (2013.01); *G02C 7/049* (2013.01)

(58) Field of Classification Search
CPC ........ G02C 1/06; G02C 1/08; G02C 2200/02; G02C 2200/08; G02C 2202/02; G02C 2202/04; G02C 2202/08; G02C 2202/12; G02C 5/02; G02C 7/046; G02C 7/048; G02C 7/08; G02C 7/108; G02C 7/14; G02C 7/16; G02B 1/041; G02B 1/105; G02B 1/14; G02B 1/18; G02B 27/0006; G02B 1/115; G02B 27/0172; G02B 3/12; G02B 1/16; G02B 2027/011; G02B 2027/0178; G02B 27/0075; G02B 27/4211; G02B 3/02; G02B 3/04; G02B 3/08; G02B 3/14; G02B 5/208; G02B 13/146; G02B 17/08; G02B 1/06; G02B 1/10; G02B 1/11; G02B 1/113; G02B 1/116; G02B 1/12; G02B 2027/0123; G02B 25/001; G02B 25/004; G02B 26/004; G02B 26/06; G02B 27/0018; G02B 27/0025; G02B 27/0037; G02B 27/2228; G02B 3/00; G02B 3/0062; G02B 3/0081; G02B 3/0087; G02B 5/00; G02B 5/1866; G02B 5/1876; G02B 5/188; G02B 5/1885; G02B 5/1895; G02B 5/286; G02B 5/3025; G02B 5/3033; G02B 6/10; A61F 2/1618; A61F 2/16; A61F 2/1613; A61F 2/1637; A61F 2/164; A61F 2/1654; A61F 2230/0006; A61F 2/1645; A61F 2002/1699; A61F 2/1451; A61F 2/1616; A61F 2/1624; A61F 2/1632; A61F 2/1648; A61F 9/045; B29D 11/00009; B29D 11/0073; B29D 11/00461; B29D 11/00028; B29D 11/00134; B29D 11/00355; B29D 11/00865; B29D 11/00038; B29D 11/00125; B29D 11/00192; B29D 11/00413; B29D 11/00519; B29D 11/00634; B29D 11/00653; B29D 11/00817; B29D 11/00826; B29D 11/00942; B29D 12/02; A61K 9/0048
USPC ........................................................ 351/159
See application file for complete search history.

(56) References Cited

U.S. PATENT DOCUMENTS

| | | |
|---|---|---|
| 8,431,624 B2 | 4/2013 | Domschke et al. |
| 9,827,250 B2 | 11/2017 | Chehab et al. |
| 2005/0254003 A1 | 11/2005 | Jani et al. |
| 2007/0159594 A9 | 7/2007 | Jani et al. |
| 2008/0291393 A1 | 11/2008 | Menezes |
| 2011/0063567 A1 | 3/2011 | Domschke et al. |
| 2013/0182215 A1 | 7/2013 | Tung |
| 2013/0293834 A1 | 11/2013 | Wang |
| 2014/0036225 A1 | 2/2014 | Chehab et al. |
| 2017/0227790 A1 | 8/2017 | Lin et al. |

FOREIGN PATENT DOCUMENTS

| | | |
|---|---|---|
| CN | 102510860 A | 6/2012 |
| CN | 103576337 A | 2/2014 |
| CN | 107037605 A | 8/2017 |
| EP | 0742464 A2 | 11/1996 |
| TW | 200643145 A | 12/2006 |
| TW | 201127881 A1 | 8/2011 |
| TW | 201410265 A | 3/2014 |

US 10,578,889 B2

CONTACT LENS PRODUCT

RELATED APPLICATIONS

The present application is a Continuation of U.S. application Ser. No. 15/401,142, filed on Jan. 9, 2017, which claims priority of Taiwan Application Serial Number 105103797, filed Feb. 4, 2016, which is herein incorporated by reference.

BACKGROUND

Technical Field

The present disclosure relates to a contact lens product. More particularly, the present disclosure relates to a contact lens product which can prevent myopia or control a progression of myopia.

Description of Related Art

According to the data of World Health Organization (WHO), the prevalence of myopia in all world countries is between 8% and 62%. However, surveys show that the prevalence of myopia in teenagers and children under 18 years old in Taiwan is up to 85%, which is significantly beyond other countries. One reason is probably due to the highly developed 3C electronic devices in recent years, which results in improper stimuluses and overuse of eyes of young children prematurely. Current researches show that once young children suffer early-onset myopia, the degree of myopia will increase with a certain speed. Current researches further show that the lower the age at which the myopia occurs is, the higher probability of becoming high myopia (greater than or equal to 6.0 D) will be. A person suffering high myopia is more likely to suffer serious complications, such as retinal detachment and glaucoma.

Therefore, if a controlling or moderating method can be conducted when the pseudomyopia is observed in the young children, the pseudomyopia can be effectively prevented from becoming myopia, and the high myopia can be further prevented.

The main cause of myopia is a variation of the optical structure of eyeballs. The optical image is mainly affected by the factors, such as cornea, lens and the length of the eyeballs. As for a normal person, lights can be precisely focused on the retina thereof so as to obtain a clearly image. However, as for a person suffering myopia, lights are focused in front of the retina thereof due to an excessive diopter (refractive myopia) or an excessive axial length of the eyeball (axial myopia), so that a blurred image is obtained. Myopia symptoms of young children can be divided into myopia and pseudomyopia, wherein the myopia occurs due to an excessive axial length of the eyeball and cannot be corrected. However, the pseudomyopia is a temporary symptom caused by excessive tension of ciliary muscle and can be corrected. Clinically, there are many methods for correcting children pseudomyopia. The main methods include wearing orthokeratology and applying long-acting mydriatics. However, the orthokeratology may result in a highly external pressure which makes the wearer uncomfortable. When the long-acting mydriatics are applied alone, a higher concentration dose is usually required. Accordingly, the probability of drug side effects is enhanced, too.

SUMMARY

According to one aspect of the present disclosure, a contact lens product includes a contact lens and a buffer solution. The contact lens is immersed in the buffer solution, and the buffer solution includes a cycloplegic agent. When a weight percentage concentration of the cycloplegic agent in the buffer solution is ConA, a visible light absorption rate of the contact lens is Avi, a blue light absorption rate of the contact lens is Abl, and an ultraviolet light absorption rate of the contact lens is Auv, the following conditions are satisfied:

0%<ConA≤1%;
0%<Avi≤80%;
0%<Abl<100%; and
0%<Auv<100%.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
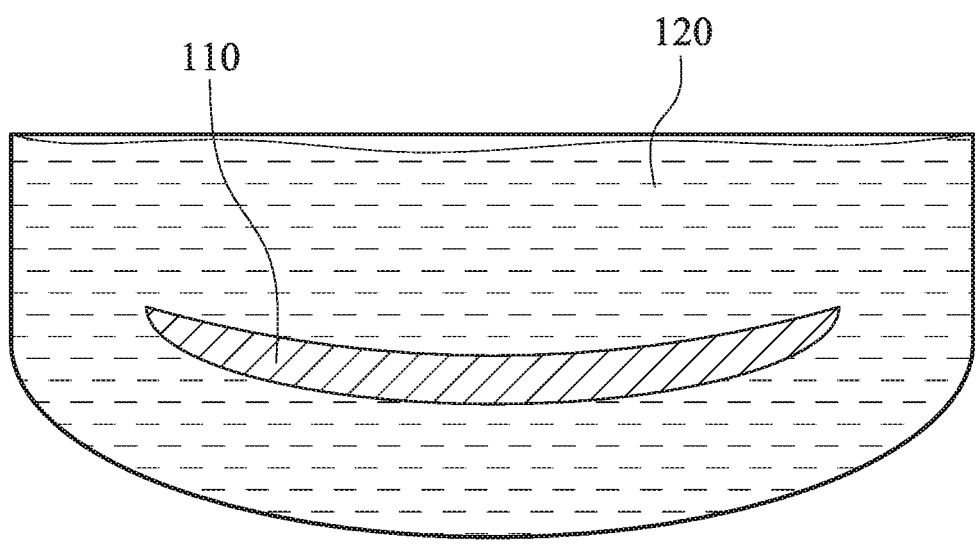
FIG. 1 is a schematic view of a contact lens product according to one embodiment of the present disclosure.

FIG. 1 is a schematic view of a contact lens product 100 according to one embodiment of the present disclosure. The contact lens product 100 includes a contact lens 110 and a buffer solution 120. The contact lens 110 is immersed in the buffer solution 120.

The buffer solution 120 includes a cycloplegic agent. When a weight percentage concentration of the cycloplegic agent in the buffer solution 120 is ConA, the following condition is satisfied: $0\% < ConA \leq 1\%$. Therefore, the concentration of the cycloplegic agent is proper, which is favorable to relax the ciliary muscle and reduce the probability of drug side effects. Alternatively, the following condition can be satisfied: $0\% < ConA \leq 0.5\%$. Alternatively, the following condition can be satisfied: $0\% < ConA \leq 0.25\%$. Alternatively, the following condition can be satisfied: $0\% < ConA \leq 0.1\%$. Alternatively, the following condition can be satisfied: $0\% < ConA \leq 0.05\%$. Alternatively, the following condition can be satisfied: $0\% < ConA \leq 0.01\%$. The buffer solution 120 can be prepared by providing a basic solution, wherein the basic solution can be a commercially available solution for immersing and preserving contact lenses. Then the cycloplegic agent is added into the basic solution to a predetermined concentration, and chemical reactions do not occur between the basic solution and the cycloplegic agent.

Figure 2:
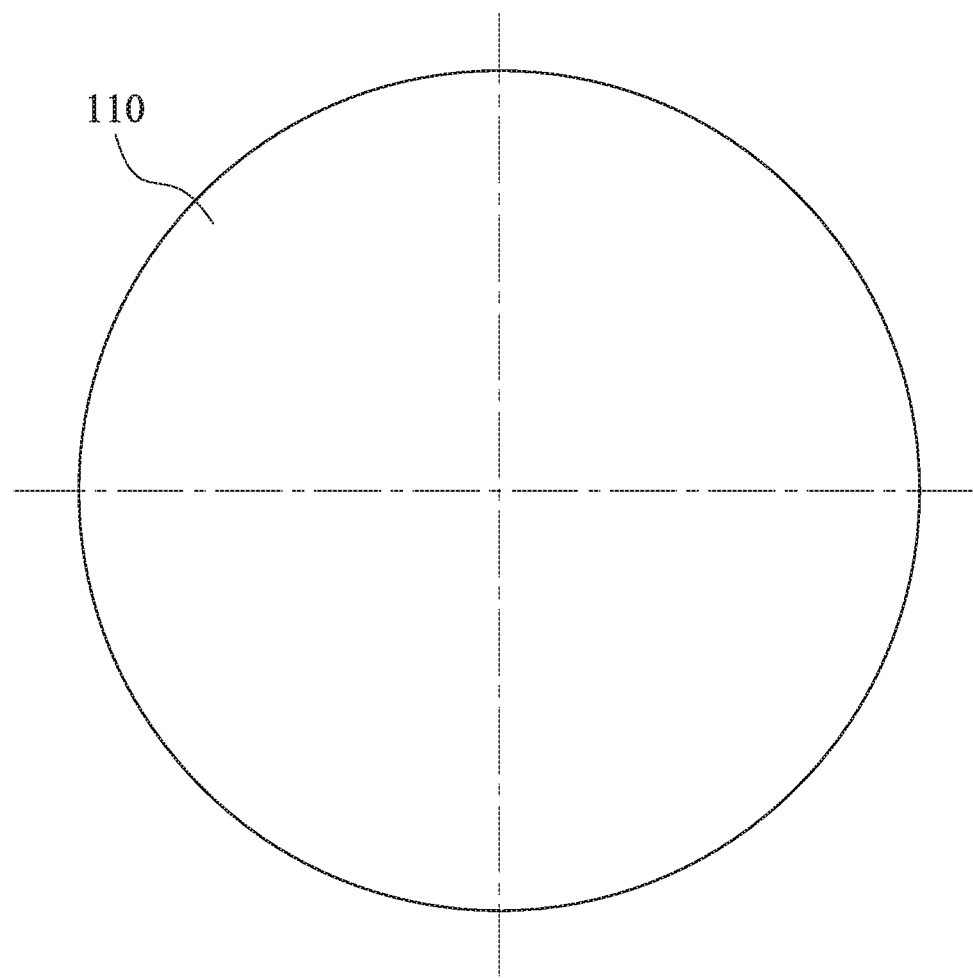
FIG. 2 is a schematic plan view of a contact lens in FIG. 1.

FIG. 2 is a schematic plan view of the contact lens 110 in FIG. 1. The contact lens 110 can be monofocal or multifocal. Furthermore, a front surface (its reference numeral is omitted) and a back surface (its reference numeral is omitted) of the contact lens 110 can be independently aspheric or spherical.

When a visible light absorption rate of the contact lens 110 is Avi, the following condition is satisfied: $0\% < Avi \leq 80\%$. Therefore, a portion of the visible lights can be absorbed so as to ease the photophobia. Alternatively, the following condition can be satisfied: $5\% \leq Avi \leq 70\%$. Alternatively, the following condition can be satisfied: $5\% \leq Avi \leq 60\%$. Alternatively, the following condition can be satisfied: $5\% \leq Avi \leq 50\%$. Alternatively, the following condition can be satisfied: $10\% \leq Avi \leq 50\%$. Alternatively, the following condition can be satisfied: $15\% \leq Avi \leq 45\%$.

When a blue light absorption rate of the contact lens 110 is Abl, the following condition is satisfied: $0\% < Abl < 100\%$. Therefore, the high-energy blue lights can be absorbed, and the probability that the retina hurt by the blue lights can be reduced. Alternatively, the following condition can be satisfied: $10\% \leq Abl \leq 80\%$. Alternatively, the following condition can be satisfied: $20\% \leq Abl \leq 70\%$. Alternatively, the following condition can be satisfied: $30\% \leq Abl \leq 70\%$. Alternatively, the following condition can be satisfied: $40\% \leq Abl \leq 60\%$. Alternatively, the following condition can be satisfied: $45\% \leq Abl \leq 60\%$.

When an ultraviolet light absorption rate of the contact lens 110 is Auv, the following condition is satisfied: $0\% < Auv < 100\%$. Therefore, the high-energy ultraviolet lights can be absorbed, and the probability that the retina hurt by the ultraviolet lights can be reduced. Alternatively, the following condition can be satisfied: $40\% \leq Auv < 100\%$. Alternatively, the following condition can be satisfied: $50\% \leq Auv < 100\%$. Alternatively, the following condition can be satisfied: $60\% \leq Auv < 100\%$. Alternatively, the following condition can be satisfied: $70\% \leq Auv < 100\%$. Alternatively, the following condition can be satisfied: $80\% \leq Auv < 100\%$.

A composition for manufacturing the contact lens 110 can include at least one light absorbing agent. The light absorbing agent can be a visible light absorbing agent or a short-wavelength light absorbing agent.

Specifically, the composition for manufacturing the contact lens 110 can include at least one of the visible light absorbing agent. Therefore, the contact lens 110 can absorb visible lights, which can prevent excessive visible lights entering into a wearer's eyes due to the enlarged pupil caused by the cycloplegic agent, and the photophobia can be eased. The visible light absorbing agent can be but is not limited to 1,4-bis[4-(2-methacryloxyethyl)phenylamino]anthraquinone or 1,4-bis[(2-methacryloxyethyl)amino]-9,10-anthraquinone. The aforementioned visible light absorbing agents can be used simultaneously or separately.

The composition for manufacturing the contact lens 110 can include at least one of the short-wavelength light absorbing agent. The short-wavelength light refers to the light with a wavelength range of 280 nm to 495 nm. Therefore, the contact lens 110 can absorb high-energy blue lights and/or ultraviolet lights, which can prevent excessive blue lights and/or ultraviolet lights entering into the wearer's eyes due to the enlarged pupil caused by the cycloplegic agent, and the probability that the retina hurt by the blue lights and/or ultraviolet lights can be reduced. The short-wavelength light absorbing agent can be but is not limited to 4-(phenyldiazenyl) phenyl methacrylate or reactive yellow 15. Alternatively, the short-wavelength light absorbing agent can be but is not limited to 2-[3-(2H-benzotriazol-2-yl)-4-hydroxyphenyl]ethyl methacrylate, 4-methacryloxy-2-hydroxybenzophenone, 2-phenylethyl acrylate, 2-phenylethyl methacrylate, 2-(2'-hydroxy-5'-methacryloxyethyl phenyl)-2H-benzotriazole, 2-(4-benzoyl-3-hydroxyphenoxy)ethyl acrylate, 3-(3-(tert-butyl)-4-hydroxy-5-(5-methoxy-2H-benzo[d][1,2,3]triazol-2-yl)phenoxy) propyl methacrylate, 1,3-bis(4-benzoyl-3-hydroxyphenoxy)-2-propyl methacrylate, 1,3-bis(4-benzoyl-3-hydroxyphenoxy)-2-propanyl acrylate or N-(4-hydroxy-3-(5-methoxy-2H-benzo[d][1,2,3]triazol-2-yl)phenyl)methacrylamide. The aforementioned short-wavelength light absorbing agents can be used simultaneously or separately.

According to the aforementioned contact lens product 100, the contact lens 110 can be made of a silicone hydrogel. Therefore, the oxygen permeability of the contact lens 110 can be enhanced, and the phenomena, such as red eyes, bloodshot eyes and swell, caused by the hypoxia of cornea can be prevented. Accordingly, the long wear comfort can be provided. The silicone hydrogel can be but is not limited to the contact lens material classified as Group V by U.S. FDA (U.S. Food and Drug Administration), such as Balafilcon A, Comfilcon A, Efrofilcon A, Enfilcon A, Galyfilcon A, Lotrafilcon A, Lotrafilcon B, Narafilcon A, Narafilcon B, Senofilcon A, Delefilcon A and Somofilcon A.

A composition for manufacturing the silicone hydrogel can include at least two monomers. The monomer can be 2-hydroxyethyl methacrylate, 3-methacryloyloxypropyltris(trimethylsilyloxy)silane, N-vinyl-2-pyrrolidinone, N,N-dimethyl acrylamide, methacrylic acid, methyl methacrylate, 3-(3-methacryloxy-2-hydroxypropoxy)propylbis(trimethylsiloxy)methylsilane or (3-acryloxy-2-hydroxypropoxypropyl)terminated polydimethylsiloxane.

The composition for manufacturing the silicone hydrogel can include 2-hydroxyethyl methacrylate, 3-methacryloxypropyltris(trimethylsilyloxy)silane, N-vinyl-2-pyrrolidinone, N,N-dimethyl acrylamide, methacrylic acid, 3-(3-methacryloxy-2-hydroxypropoxy)propylbis (trimethylsiloxy)methylsilane, ethylene glycol dimethacrylate, 2-hydroxy-2-methyl-propiophenone and isopropyl alcohol.

Preferably, a weight percentage concentration of the ingredients of the composition for manufacturing the silicone hydrogel can be as follows. The weight percentage concentration of the 2-hydroxyethyl methacrylate is 0.05% to 25%, the weight percentage concentration of the 3-methacryloyloxypropyltris(trimethylsilyloxy)silane is 0.1% to 40%, the weight percentage concentration of the N-vinyl-2-pyrrolidinone is 0.1% to 35%, the weight percentage concentration of the N,N-dimethyl acrylamide is 0.1% to 40%, the weight percentage concentration of the methacrylic acid is 0.01% to 5%, the weight percentage concentration of the 3-(3-methacryloxy-2-hydroxypropoxy)propylbis(trimethylsiloxy)methylsilane is 0.1% to 30%, the weight percentage concentration of the ethylene glycol dimethacrylate is 0.01% to 5%, the weight percentage concentration of the 2-hydroxy-2-methyl-propiophenone is 0.01% to 5%, and the weight percentage concentration of the isopropyl alcohol is 0.1% to 30%.

More preferably, the weight percentage concentration of the ingredients of the composition for manufacturing the silicone hydrogel can be as follows. The weight percentage concentration of the 2-hydroxyethyl methacrylate is 0.1% to 10%, the weight percentage concentration of the 3-methacryloyloxypropyltris(trimethylsilyloxy)silane is 1% to 40%, the weight percentage concentration of the N-vinyl-2-pyrrolidinone is 1% to 35%, the weight percentage concentration of the N,N-dimethyl acrylamide is 1% to 20%, the weight percentage concentration of the methacrylic acid is 0.1% to 2%, the weight percentage concentration of the 3-(3-methacryloxy-2-hydroxypropoxy)propylbis(trimethylsiloxy)methylsilane is 1% to 30%, the weight percentage concentration of the ethylene glycol dimethacrylate is 0.1% to 2%, the weight percentage concentration of the 2-hydroxy-2-methyl-propiophenone is 0.1% to 2%, and the weight percentage concentration of the isopropyl alcohol is 1% to 20%.

The composition for manufacturing the silicone hydrogel can include 2-hydroxyethyl methacrylate, 3-methacryloyloxypropyltris(trimethylsilyloxy)silane, N-vinyl-2-pyrrolidinone, N,N-dimethyl acrylamide, (3-acryloxy-2-hydroxypropoxypropyl)terminated polydimethylsiloxane, ethylene glycol dimethacrylate, 2-hydroxy-2-methyl-propiophenone and 1-hexanol.

Preferably, a weight percentage concentration of the ingredients of the composition for manufacturing the silicone hydrogel can be as follows. The weight percentage concentration of the 2-hydroxyethyl methacrylate is 0.05% to 25%, the weight percentage concentration of the 3-methacryloyloxypropyltris(trimethylsilyloxy)silane is 0.1% to 40%, the weight percentage concentration of the N-vinyl-2-pyrrolidinone is 0.1% to 35%, the weight percentage concentration of the N,N-dimethyl acrylamide is 0.1% to 40%, the weight percentage concentration of the (3-acryloxy-2-hydroxypropoxypropyl)terminated polydimethylsiloxane is 0.1% to 40%, the weight percentage concentration of the ethylene glycol dimethacrylate is 0.01% to 5%, the weight percentage concentration of the 2-hydroxy-2-methyl-propiophenone is 0.01% to 5%, and the weight percentage concentration of the 1-hexanol is 0.1% to 30%.

More preferably, the weight percentage concentration of the ingredients of the composition for manufacturing the silicone hydrogel can be as follows. The weight percentage concentration of the 2-hydroxyethyl methacrylate is 0.1% to 10%, the weight percentage concentration of the 3-methacryloyloxypropyltris(trimethylsilyloxy)silane is 1% to 40%, the weight percentage concentration of the N-vinyl-2-pyrrolidinone is 1% to 35%, the weight percentage concentration of the N,N-dimethyl acrylamide is 1% to 20%, the weight percentage concentration of the (3-acryloxy-2-hydroxypropoxypropyl)terminated polydimethylsiloxane is 1% to 40%, the weight percentage concentration of the ethylene glycol dimethacrylate is 0.1% to 2%, the weight percentage concentration of the 2-hydroxy-2-methyl-propiophenone is 0.1% to 2%, and the weight percentage concentration of the 1-hexanol is 1% to 30%.

The composition for manufacturing the silicone hydrogel can include 2-hydroxyethyl methacrylate, 3-methacryloyloxypropyltris(trimethylsilyloxy)silane, N-vinyl-2-pyrrolidinone, N,N-dimethyl acrylamide, methyl methacrylate, polysiloxane macromer, 2-hydroxy-2-methyl-propiophenone and ethanol.

Preferably, a weight percentage concentration of the ingredients of the composition for manufacturing the silicone hydrogel can be as follows. The weight percentage concentration of the 2-hydroxyethyl methacrylate is 0.05% to 25%, the weight percentage concentration of the 3-methacryloyloxypropyltris(trimethylsilyloxy)silane is 0.1% to 40%, the weight percentage concentration of the N-vinyl-2-pyrrolidinone is 0.1% to 35%, the weight percentage concentration of the N,N-dimethyl acrylamide is 0.1% to 40%, the weight percentage concentration of the methyl methacrylate is 0.1% to 20%, the weight percentage concentration of the polysiloxane macromer is 0.1% to 40%, the weight percentage concentration of the 2-hydroxy-2-methyl-propiophenone is 0.01% to 5%, and the weight percentage concentration of the ethanol is 0.1% to 30%.

More preferably, the weight percentage concentration of the ingredients of the composition for manufacturing the silicone hydrogel can be as follows. The weight percentage concentration of the 2-hydroxyethyl methacrylate is 0.1% to 10%, the weight percentage concentration of the 3-methacryloyloxypropyltris(trimethylsilyloxy)silane is 1% to 40%, the weight percentage concentration of the N-vinyl-2-pyrrolidinone is 1% to 35%, the weight percentage concentration of the N,N-dimethyl acrylamide is 1% to 20%, the weight percentage concentration of the methyl methacrylate is 1% to 10%, the weight percentage concentration of the polysiloxane macromer is 1% to 40%, the weight percentage concentration of the 2-hydroxy-2-methyl-propiophenone is 0.1% to 2%, and the weight percentage concentration of the ethanol is 1% to 20%.

Each of the aforementioned compositions for manufacturing the silicone hydrogel can further include a visible light absorbing agent. Preferably, the weight percentage concentration of the visible light absorbing agent of the composition for manufacturing the silicone hydrogel is 0.01% to 0.5%. More preferably, the weight percentage concentration of the visible light absorbing agent of the composition for manufacturing the silicone hydrogel is 0.01% to 0.25%. Each of the aforementioned compositions for manufacturing the silicone hydrogel can further include a short-wavelength light absorbing agent. Preferably, the weight percentage concentration of the short-wavelength light absorbing agent of the composition for manufacturing the silicone hydrogel is 0.01% to 10%. More preferably, the weight percentage concentration of the short-wavelength light absorbing agent of the composition for manufacturing the silicone hydrogel is 0.1% to 5%. Furthermore, the composition for manufacturing the silicone hydrogel can include one of the visible light absorbing agent and the short-wavelength light absorbing agent, or can include both of the visible light absorbing agent and the short-wavelength light absorbing agent.

By adjusting the ratio of the ingredients of the composition for manufacturing the silicone hydrogel, an oxygen permeability and a hardness of the contact lens 110 can be effectively enhanced. Furthermore, the composition for manufacturing the silicone hydrogel can selectively include other ingredients according to practical needs.

According to the aforementioned contact lens product 100, the contact lens 110 can be made of a hydrogel. Therefore, the moisture, smoothness and softness of the contact lens 110 can be maintained, and is capable of long wear. Furthermore, the foreign body sensation can be avoided when wearing the contact lens 110. The hydrogel can be but is not limited to the contact lens material classified as Group I by U.S. FDA, i.e., nonionic polymers having a low water content (less than 50 wt %), such as Helflcon A&B, Hioxifilcon B, Mafilcon, Polymacon, Tefilcon and Tetrafilcon A. Alternatively, the hydrogel can be but is not limited to the contact lens material classified as Group II by U.S. FDA, i.e., nonionic polymers having a high water content (greater than 50 wt %), such as Acofilcon A, Alfafilcon A, Hilafilcon B, Hioxifilcon A, Hioxifilcon B, Hioxifilcon D, Nelfilcon A, Nesofilcon A, Omafilcon A and Samfilcon A. Alternatively, the hydrogel can be but is not limited to the contact lens material classified as Group III by U.S. FDA, i.e., ionic polymers having a low water content (less than 50 wt %), such as Deltafilcon A. Alternatively, the hydrogel can be but is not limited to the contact lens material classified as Group IV by U.S. FDA, i.e., ionic polymers having a high water content (greater than 50 wt %), such as Etafilcon A, Focofilcon A, Methafilcon A, Methafilcon B, Ocufilcon A, Ocufilcon B, Ocufilcon C, Ocufilcon D, Ocufilcon E, Phemfilcon A and Vifilcon A.

A composition for manufacturing the hydrogel can include at least two monomers. The monomer can be 2-hydroxyethyl methacrylate, methacrylic acid, glycerol monomethacrylate or N-vinyl-2-pyrrolidinone.

The composition for manufacturing the hydrogel can include 2-hydroxyethyl methacrylate, methacrylic acid, ethylene glycol dimethacrylate, 1,1,1-trimethylol propane trimethacrylate, 2-hydroxy-2-methyl-propiophenone and glycerol.

Preferably, a weight percentage concentration of the ingredients of the composition for manufacturing the hydrogel can be as follows. The weight percentage concentration of the 2-hydroxyethyl methacrylate is 10% to 96%, the weight percentage concentration of the methacrylic acid is 0.01% to 5%, the weight percentage concentration of the ethylene glycol dimethacrylate is 0.01% to 5%, the weight percentage concentration of the 1,1,1-trimethylol propane trimethacrylate is 0.01% to 5%, the weight percentage concentration of the 2-hydroxy-2-methyl-propiophenone is 0.01% to 5%, and the weight percentage concentration of the glycerol is 0.1% to 30%.

More preferably, the weight percentage concentration of the ingredients of the composition for manufacturing the hydrogel can be as follows. The weight percentage concentration of the 2-hydroxyethyl methacrylate is 40% to 96%, the weight percentage concentration of the methacrylic acid is 0.1% to 2%, the weight percentage concentration of the ethylene glycol dimethacrylate is 0.1% to 2%, the weight percentage concentration of the 1,1,1-trimethylol propane trimethacrylate is 0.1% to 2%, the weight percentage concentration of the 2-hydroxy-2-methyl-propiophenone is 0.1% to 2%, and the weight percentage concentration of the glycerol is 1% to 20%.

The composition for manufacturing the hydrogel can include 2-hydroxyethyl methacrylate, glycerol monomethacrylate, ethylene glycol dimethacrylate, 1,1,1-trimethylol propane trimethacrylate, 2-hydroxy-2-methyl-propiophenone and glycerol.

Preferably, a weight percentage concentration of the ingredients of the composition for manufacturing the hydrogel can be as follows. The weight percentage concentration of the 2-hydroxyethyl methacrylate is 10% to 94.85%, the weight percentage concentration of the glycerol monomethacrylate is 5% to 60%, the weight percentage concentration of the ethylene glycol dimethacrylate is 0.01% to 5%, the weight percentage concentration of the 1,1,1-trimethylol propane trimethacrylate is 0.01% to 5%, the weight percentage concentration of the 2-hydroxy-2-methyl-propiophenone is 0.01% to 5%, and the weight percentage concentration of the glycerol is 0.1% to 30%.

More preferably, the weight percentage concentration of the ingredients of the composition for manufacturing the hydrogel can be as follows. The weight percentage concentration of the 2-hydroxyethyl methacrylate is 40% to 79.4%, the weight percentage concentration of the glycerol monomethacrylate is 20% to 50%, the weight percentage concentration of the ethylene glycol dimethacrylate is 0.1% to 2%, the weight percentage concentration of the 1,1,1-trimethylol propane trimethacrylate is 0.1% to 2%, the weight percentage concentration of the 2-hydroxy-2-methyl-propiophenone is 0.1% to 2%, and the weight percentage concentration of the glycerol is 1% to 20%.

The composition for manufacturing the hydrogel can include 2-hydroxyethyl methacrylate, N-vinyl-2-pyrrolidinone, ethylene glycol dimethacrylate, 2-hydroxy-2-methyl-propiophenone and glycerol.

Preferably, a weight percentage concentration of the ingredients of the composition for manufacturing the hydrogel can be as follows. The weight percentage concentration of the 2-hydroxyethyl methacrylate is 10% to 96%, the weight percentage concentration of the N-vinyl-2-pyrrolidinone is 0.1% to 25%, the weight percentage concentration of the ethylene glycol dimethacrylate is 0.01% to 5%, the weight percentage concentration of the 2-hydroxy-2-methyl-propiophenone is 0.01% to 5%, and the weight percentage concentration of the glycerol is 0.1% to 30%.

More preferably, the weight percentage concentration of the ingredients of the composition for manufacturing the hydrogel can be as follows. The weight percentage concentration of the 2-hydroxyethyl methacrylate is 40% to 96%, the weight percentage concentration of the N-vinyl-2-pyrrolidinone is 0.1% to 10%, the weight percentage concentration of the ethylene glycol dimethacrylate is 0.1% to 2%, the weight percentage concentration of the 2-hydroxy-2-methyl-propiophenone is 0.1% to 2%, and the weight percentage concentration of the glycerol is 1% to 20%.

Each of the aforementioned compositions for manufacturing the hydrogel can further include a visible light absorbing agent. Preferably, the weight percentage concentration of the visible light absorbing agent of the composition for manufacturing the hydrogel is 0.01% to 0.5%. More preferably, the weight percentage concentration of the visible light absorbing agent of the composition for manufacturing the hydrogel is 0.01% to 0.25%. Each of the aforementioned compositions for manufacturing the hydrogel can further include a short-wavelength light absorbing agent. Preferably, the weight percentage concentration of the short-wavelength light absorbing agent of the composition for manufacturing the hydrogel is 0.01% to 10%. More preferably, the weight percentage concentration of the short-wavelength light absorbing agent of the composition for manufacturing the hydrogel is 0.1% to 5%. Furthermore, the composition for manufacturing the hydrogel can include one of the visible light absorbing agent and the short-wavelength light absorbing agent, or can include both of the visible light absorbing agent and the short-wavelength light absorbing agent.

By adjusting the ratio of the ingredients of the composition for manufacturing the hydrogel, a water content and a softness of the contact lens 110 can be effectively enhanced. Furthermore, the composition for manufacturing the hydrogel can selectively include other ingredients according to practical needs. The monomers used in the composition for manufacturing the hydrogel and the monomers used in the composition for silicone hydrogel, such as 2-hydroxyethyl methacrylate, methacrylic acid, glycerol monomethacrylate, N-vinyl-2-pyrrolidinone, 3-methacryloyloxypropyltris(trimethylsilyloxy)silane, N,N-dimethyl acrylamide, 3-(3-methacryloxy-2-hydroxypropoxy)propylbis(trimethylsiloxy) methylsilane, (3-acryloxy-2-hydroxypropoxypropyl) terminated polydimethylsiloxane and methyl methacrylate can be interchanged according to practical needs.

Figure 3:
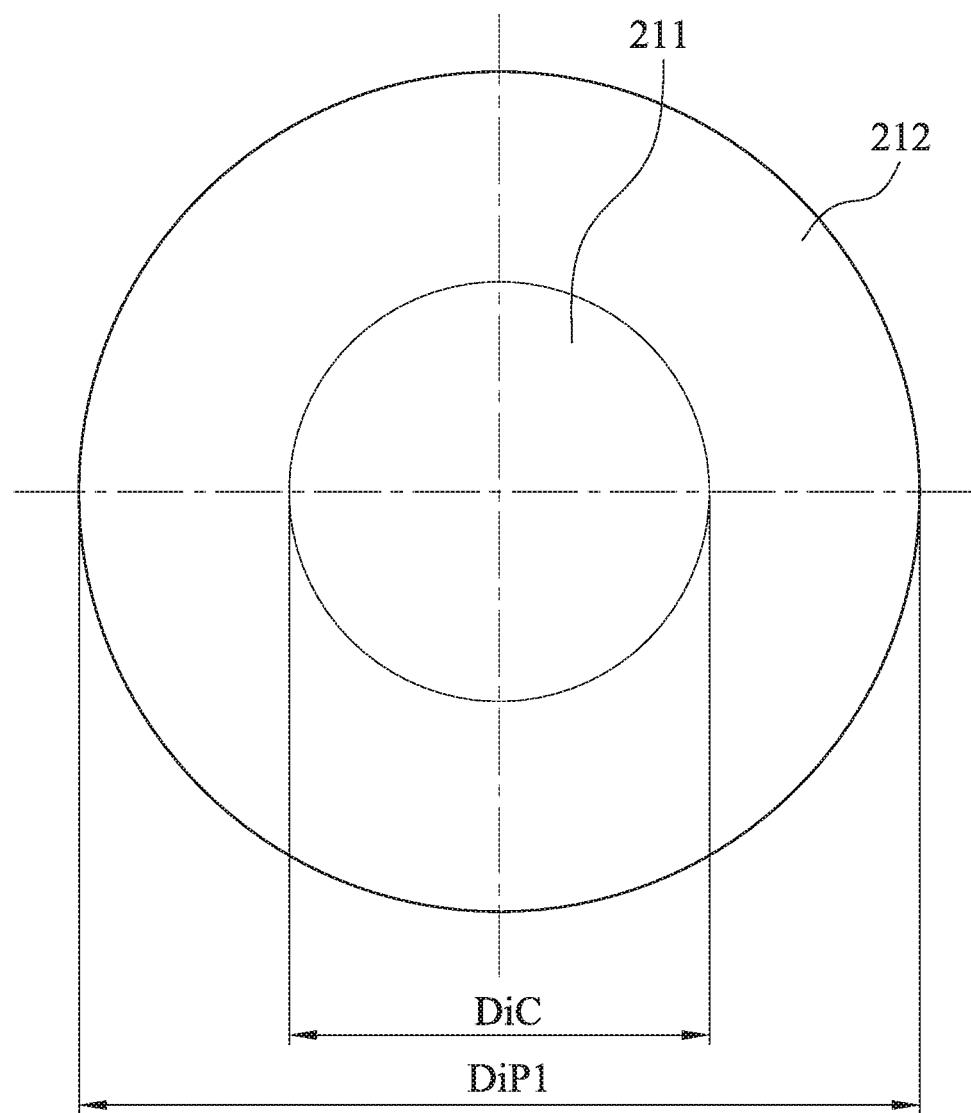
FIG. 3 is a schematic plan view of a contact lens according to another embodiment of the present disclosure.

FIG. 3 is a schematic plan view of a contact lens 210 according to another embodiment of the present disclosure. The contact lens 210 includes a central region 211 and a first annular region 212. The first annular region 212 surrounds the central region 211. A diopter of the first annular region 212 is different from a diopter of the central region 211. Therefore, the contact lens 210 is featured with multi-focus function, the peripheral image can be formed in front of the retina, which can moderate the increase of the axial length of the eyeball, and the exacerbation of myopia can be prevented. According to one example of the present disclosure, the diopter of the central region 211 is fixed. Moreover, the first annular region 212 can concentrically surround the central region 211.

At least one of the central region 211 and the first annular region 212 of the contact lens 210 is aspheric. Therefore, it is favorable to design the first annular region 212 with a gradient diopter.

When a diameter of the central region 211 of the contact lens 210 is DiC, the following condition can be satisfied: 4 mm≤DiC≤10 mm. Therefore, the diameter can be flexibly adjusted according to the pupil size of different physiological states, so that the accuracy for correcting myopia provided by the central region 211 can be enhanced, and the scene can be completely and clearly focused on retina. Preferably, the following condition can be satisfied: 5 mm≤DiC≤9 mm.

When an outer diameter of the first annular region 212 of the contact lens 210 is DiP1, and the following condition can be satisfied: 6 mm≤DiP1≤17 mm. Therefore, the outer diameter can be flexibly adjusted according to the size of palpebral fissure, so that a proper comfort and fitness of the contact lens 210 can be provided, and the wearing stability of the contact lens 210 can be enhanced. Preferably, the following condition can be satisfied: 7 mm≤DiP1≤15 mm.

When the diameter of the central region 211 of the contact lens 210 is DiC, and the outer diameter of the first annular region 212 of the contact lens 210 is DiP1, the following condition can be satisfied: 0.15≤DiC/DiP1<1. Therefore, the value of DiC/DiP1 is proper, which is favorable to design the contact lens 210 according to the physiological state of individual eyeball. Accordingly, it is favorable to correct myopia.

When the diopter of the central region 211 of the contact lens 210 is PowC, the following condition can be satisfied: −6.00 D≤PowC≤−0.25 D. Therefore, a proper correction for myopia can be provided according to the need of users. Accordingly, a clear image can be provided.

When a maximum diopter of the first annular region 212 of the contact lens 210 is PowP1, the following condition can be satisfied: −5.50 D≤PowP1≤−0.50 D. Therefore, the maximal diopter of the first annular region 212 can be properly designed, which is favorable to correct myopia.

When the diopter of the central region 211 of the contact lens 210 is PowC, and the maximum diopter of the first annular region 212 of the contact lens 210 is PowP1, the following condition can be satisfied: |PowC−PowP1|≤12 D. Therefore, it is favorable to correct myopia. Furthermore, the increase degree of the diopter of the first annular region 212 can be moderated, so that the discomfort resulted from the excessive increase degree of the diopter can be avoided. Alternatively, the following condition can be satisfied: |PowC−PowP1|≤10 D. Alternatively, the following condition can be satisfied: |PowC−PowP1|≤5 D. Alternatively, the following condition can be satisfied: |PowC−PowP1|≤3 D. Alternatively, the following condition can be satisfied: |PowC−PowP1|≤2 D. Alternatively, the following condition can be satisfied: |PowC−PowP1|≤1.5 D. Alternatively, the following condition can be satisfied: |PowC−PowP1|≤1 D. Alternatively, the following condition can be satisfied: |PowC−PowP1|≤0.5 D. Alternatively, the following condition can be satisfied: |PowC−PowP1|≤0.25 D.

The other properties of the contact lens 210 can be the same as that of the contact lens 110, and will not be repeated herein.

Figure 4:
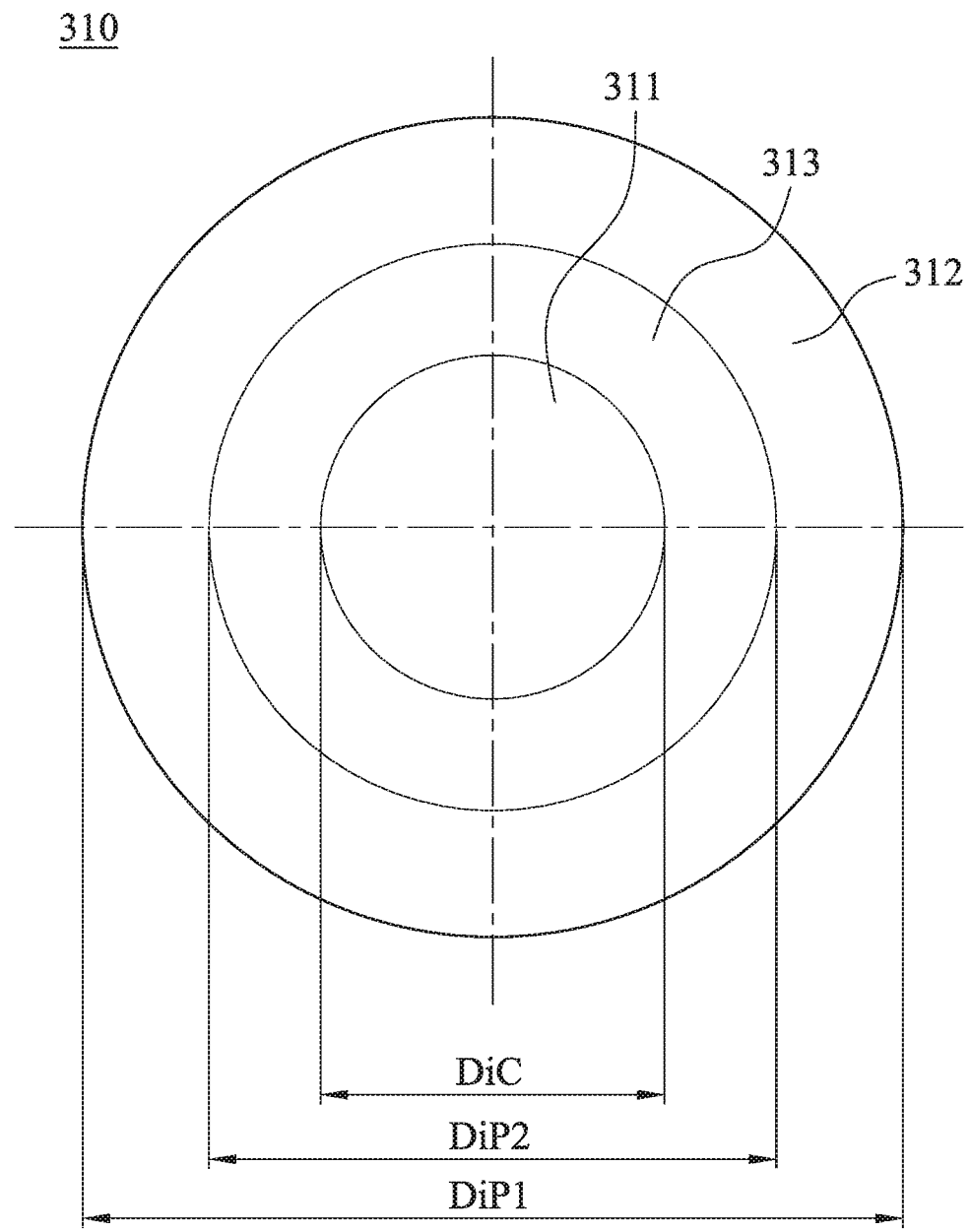
FIG. 4 is a schematic plan view of a contact lens according to yet another embodiment of the present disclosure.

FIG. 4 is a schematic plan view of a contact lens 310 according to yet another embodiment of the present disclosure. The contact lens 310 includes a central region 311, a first annular region 312 and a second annular region 313. The central region 311, the second annular region 313 and the first annular region 312 are sequentially connected from a center of the contact lens 310 to a periphery of the contact lens 310. A diameter of the central region 311 of the contact lens 310 is DiC. An outer diameter of the first annular region 312 of the contact lens 310 is DiP1. An outer diameter of the second annular region 313 of the contact lens 310 is DiP2. A diopter of the second annular region 313 is different from a diopter of the central region 311. Therefore, the contact lens 310 is featured with multi-focus function, the peripheral image can be formed in front of the retina, which can moderate the increase of the axial length of the eyeball, and the exacerbation of myopia can be prevented. According to one example of the present disclosure, the diopter of the central region 311 is fixed. Moreover, the central region 311, the second annular region 313 and the first annular region 312 can be concentric.

At least one of the central region 311, the first annular region 312 and the second annular region 313 is aspheric. Therefore, it is favorable to design the first annular region 312 and/or the second annular region 313 with a gradient diopter.

When the outer diameter of the second annular region 313 of the contact lens 310 is DiP2, the following condition can be satisfied: 5 mm≤DiP2≤13 mm. Therefore, the increase degree of the diopter can be moderated. Preferably, the following condition can be satisfied: 6 mm≤DiP2≤12 mm.

When the diameter of the central region 311 of the contact lens 310 is DiC, the outer diameter of the second annular region 313 of the contact lens 310 is DiP2, the following condition can be satisfied: 0.2≤DiC/DiP2<1. Therefore, the increase degree of the diopter of the second annular region 313 can be moderated, so that the discomfort resulted from the excessive increase degree of the diopter can be avoided.

The other properties of the contact lens 310 can be the same as that of the contact lens 110 or the contact lens 210, and will not be repeated herein.

Figure 5:
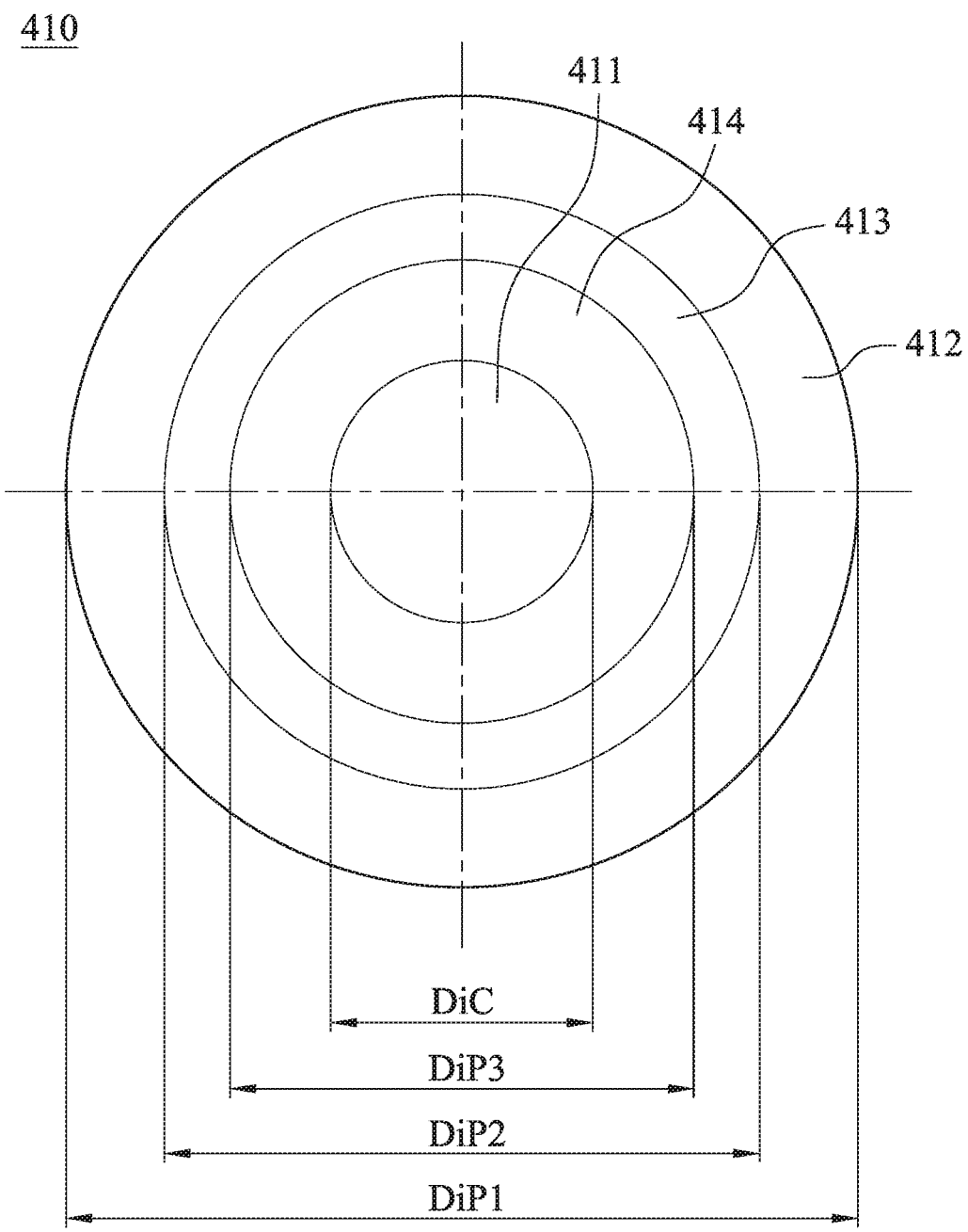
FIG. 5 is a schematic plan view of a contact lens according to further another embodiment of the present disclosure.

FIG. 5 is a schematic plan view of a contact lens 410 according to further another embodiment of the present disclosure. The contact lens 410 includes a central region 411, a first annular region 412, a second annular region 413 and a third annular region 414. The central region 411, the third annular region 414, the second annular region 413 and the first annular region 412 are sequentially connected from a center of the contact lens 410 to a periphery of the contact lens 410. A diameter of the central region 411 of the contact lens 410 is DiC. An outer diameter of the first annular region 412 of the contact lens 410 is DiP1. An outer diameter of the second annular region 413 of the contact lens 410 is DiP2. An outer diameter of the third annular region 414 of the contact lens 410 is DiP3. A diopter of the third annular region 414 is different from a diopter of the central region 411. A diopter of the second annular region 413 is different from the diopter of the central region 411. A diopter of the first annular region 412 is different from the diopter of the central region 411. Therefore, the contact lens 410 is featured with multi-focus function, the peripheral image can be formed in front of the retina, which can moderate the increase of the axial length of the eyeball, and the exacerbation of myopia can be prevented. According to one example of the present disclosure, the diopter of the central region 411 is fixed. Moreover, the central region 411, the third annular region 414, the second annular region 413 and the first annular region 412 can be concentric.

As shown in FIGS. 3-5, the contact lens (210, 310, 410) according to the present disclosure can have at least one annular region (the first annular region (212, 312, 412), the second annular region (313, 413), the third annular region (414)) surrounding the central region (211, 311, 411). The number and the diopter of the annular region can be flexibly adjusted according to the physiological state of individual eyeball, so that the effect of correcting myopia can be enhanced. Accordingly, the myopia can be effectively prevented or controlled.

1st Example

In the 1st example, a contact lens product (not shown) includes a contact lens and a buffer solution. The contact lens is immersed in the buffer solution, and the buffer solution includes a cycloplegic agent. The contact lens includes a central region and a first annular region. The first annular region concentrically surrounds the central region. A diopter of the first annular region is different from a diopter of the central region. The schematic view of the contact lens product of the 1st example can refer to FIG. 1. The structure of the contact lens of the 1st example can refer to FIG. 3.

In the contact lens product according to the 1st example, when a weight percentage concentration of the cycloplegic agent in the buffer solution is ConA, the following condition is satisfied: ConA=1.0%.

In the contact lens product according to the 1st example, a diameter of the central region of the contact lens is DiC, an outer diameter of the first annular region of the contact lens is DiP1, the diopter of the central region of the contact lens is PowC, a maximal diopter of the first annular region of the contact lens is PowP1, and the value of DiC, DiP1, DiC/DiP1, PowC, PowP1 and |PowC−PowP1| of the 1st example are listed in Table 1.

TABLE 1

| 1st example | | | |
|---|---|---|---|
| DiC (mm) | 5.00 | PowC (D) | −0.25 |
| DiP1 (mm) | 13.00 | PowP1 (D) | 0.25 |
| DiC/DiP1 | 0.38 | |PowC − PowP1| (D) | 0.50 |

Figure 6:
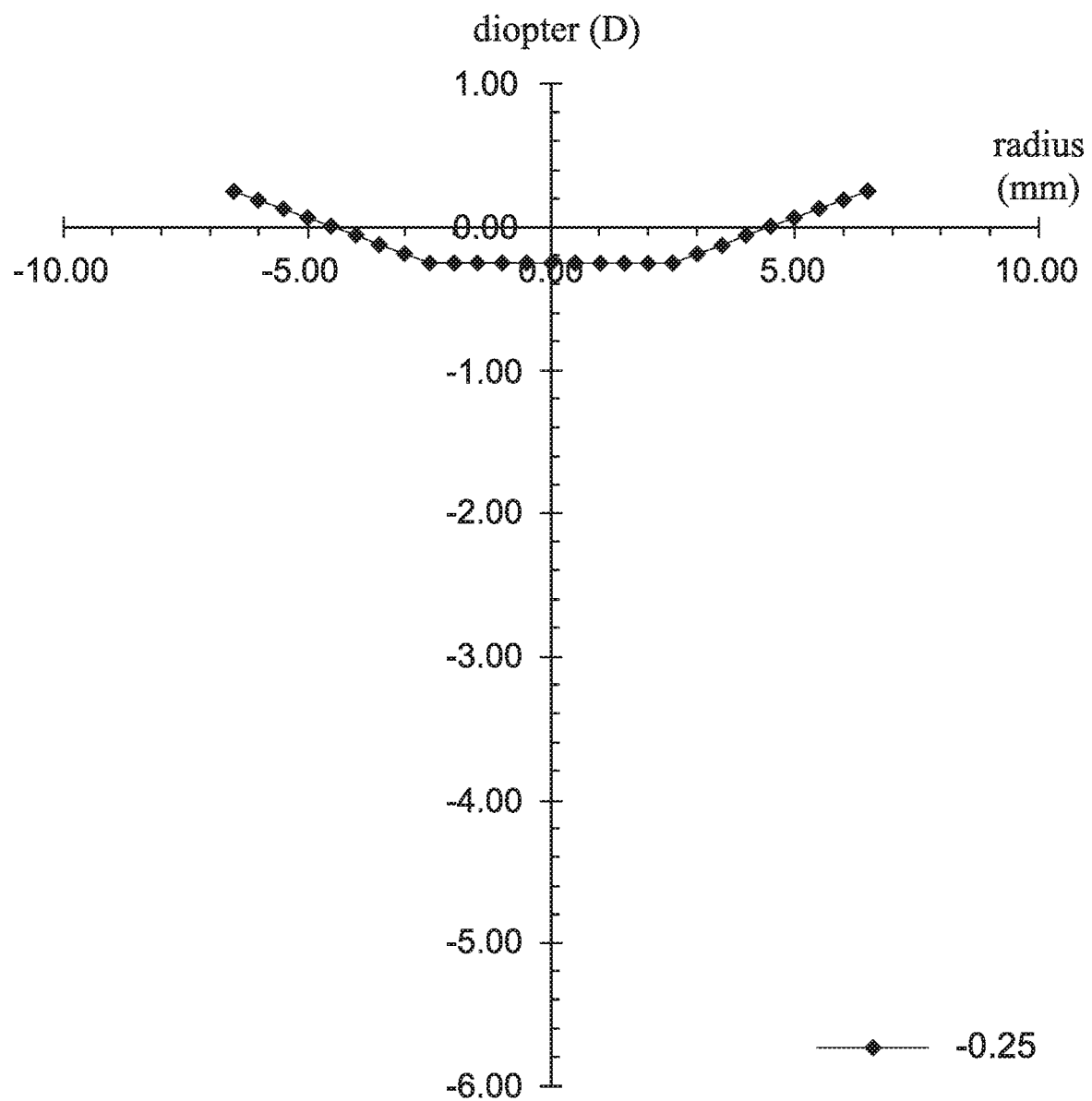
FIG. 6 shows a relationship between a radius and a diopter of a contact lens of the 1st example.

Please refer to Table 2 and FIG. 6 simultaneously. The radius and the correspondent diopter of the contact lens of the 1st example are listed in Table 2. FIG. 6 shows a relationship between the radius and the diopter of the contact lens of the 1st example (the negative radius having an opposite direction with the positive radius). As shown in Table 2 and FIG. 6, the diopter of the central region is fixed, and the diopter of the first annular region is different from the diopter of the central region. Specifically, the diopter of the first annular region is greater than the diopter of the central region, and the diopter of the first annular region increases when away from the central region.

TABLE 2

| 1st example | |
|---|---|
| radius (mm) | diopter (D) |
| −6.50 | 0.25 |
| −6.00 | 0.19 |
| −5.50 | 0.13 |
| −5.00 | 0.06 |
| −4.50 | 0.00 |
| −4.00 | −0.06 |
| −3.50 | −0.13 |
| −3.00 | −0.19 |
| −2.50 | −0.25 |
| −2.00 | −0.25 |
| −1.50 | −0.25 |
| −1.00 | −0.25 |
| −0.50 | −0.25 |
| 0.00 | −0.25 |
| 0.50 | −0.25 |
| 1.00 | −0.25 |
| 1.50 | −0.25 |
| 2.00 | −0.25 |
| 2.50 | −0.25 |
| 3.00 | −0.19 |
| 3.50 | −0.13 |
| 4.00 | −0.06 |
| 4.50 | 0.00 |
| 5.00 | 0.06 |
| 5.50 | 0.13 |
| 6.00 | 0.19 |
| 6.50 | 0.25 |

In the 1st example, the contact lens is made of hydrogel. A composition for manufacturing the hydrogel of the 1 st example is listed in Table 3A.

TABLE 3A

| function | Ingredient | Content (wt %) |
|---|---|---|
| monomer | 2-hydroxyethyl methacrylate | 82 |
| monomer | methacrylic acid | 2.2 |
| crosslinking agent | ethylene glycol dimethacrylate | 0.4 |

TABLE 3A-continued

| function | Ingredient | Content (wt %) |
|---|---|---|
| crosslinking agent | 1,1,1-trimethylol propane trimethacrylate | 0.2 |
| initiator | 2-hydroxy-2-methyl-propiophenone | 0.5 |
| diluent | glycerol | 13.25 |
| visible light absorbing agent | 1,4-bis[4-(2-methacryloxyethyl)phenyl-amino]anthraquinone | 0.25 |
| short-wavelength light absorbing agent | 2-(2'-hydroxy-5'-methacryloxyethylphenyl)-2H-benzotriazole | 1.2 |

In the contact lens product according to the 1st example, a visible light absorption rate of the contact lens is Avi, a blue light absorption rate of the contact lens is Abl, an ultraviolet light absorption rate of the contact lens is Auv, and the value of Avi, Abl and Auv of the 1st example are listed in Table 3B.

TABLE 3B

| 1st example | | |
|---|---|---|
| Avi (%) | Abl (%) | Auv(%) |
| 17.40 | 10.50 | 72.70 |

The visible light (with a wavelength ranging from 380 nm to 700 nm) absorption rate can be calculated by the following formula: (1−an average transmittance of the wavelength ranging from 380 nm to 700 nm)×100%. The blue light (with a wavelength ranging from 380 nm to 495 nm) absorption rate can be calculated by the following formula: (1−an average transmittance of the wavelength ranging from 380 nm to 495 nm)×100%. The ultraviolet light (with a wavelength ranging from 280 nm to 380 nm) absorption rate can be calculated by the following formula: (1−an average transmittance of the wavelength ranging from 280 nm to 380 nm)×100%. The aforementioned formulas can be applied to calculate the visible light absorption rate, the blue light absorption rate and the ultraviolet light absorption rate of the following examples and comparative examples, and will not be repeated hereinafter.

1st Comparative Example

The main difference between the 1st comparative example and the 1st example is the 1st comparative example in lack of the visible light absorbing agent and the short-wavelength light absorbing agent. In the 1st comparative example, the contact lens is made of hydrogel. A composition for manufacturing the hydrogel of the 1st comparative example is listed in Table 4A.

TABLE 4A

| function | Ingredient | Content (wt %) |
|---|---|---|
| monomer | 2-hydroxyethyl methacrylate | 83.45 |
| monomer | methacrylic acid | 2.2 |
| crosslinking agent | ethylene glycol dimethacrylate | 0.4 |
| crosslinking agent | 1,1,1-trimethylol propane trimethacrylate | 0.2 |
| initiator | 2-hydroxy-2-methyl-propiophenone | 0.5 |
| diluent | glycerol | 13.25 |

In the contact lens product according to the 1st comparative example, a visible light absorption rate of the contact lens is Avi, a blue light absorption rate of the contact lens is Abl, an ultraviolet light absorption rate of the contact lens is Auv, and the value of Avi, Abl and Auv of the 1st comparative example are listed in Table 4B.

TABLE 4B

| 1st comparative example | | |
|---|---|---|
| Avi (%) | Abl (%) | Auv(%) |
| 4.90 | 2.35 | 9.80 |

The other properties of the contact lens of the 1st comparative example are the same as that of the 1st example, and will not be repeated herein.

2nd Example

In the 2nd example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 2nd example can refer to FIG. 1. The structure of the contact lens of the 2nd example can refer to FIG. 4.

In the contact lens product according to the 2nd example, when a weight percentage concentration of the cycloplegic agent in the buffer solution is ConA, the following condition is satisfied: ConA=0.75%.

In the contact lens product according to the 2nd example, a diameter of the central region of the contact lens is DiC, an outer diameter of the first annular region of the contact lens is DiP1, an outer diameter of the second annular region of the contact lens is DiP2, a diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 2nd example are listed in Table 5.

TABLE 5

| 2nd example | | | |
|---|---|---|---|
| DiC (mm) | 5.00 | PowC (D) | −0.50 |
| DiP1 (mm) | 16.00 | PowP1 (D) | 0.50 |
| DiP2 (mm) | 13.00 | PowP2 (D) | 0.50 |
| DiC/DiP1 | 0.31 | |PowC − PowP1| (D) | 1.00 |
| DiC/DiP2 | 0.38 | | |

Figure 7:
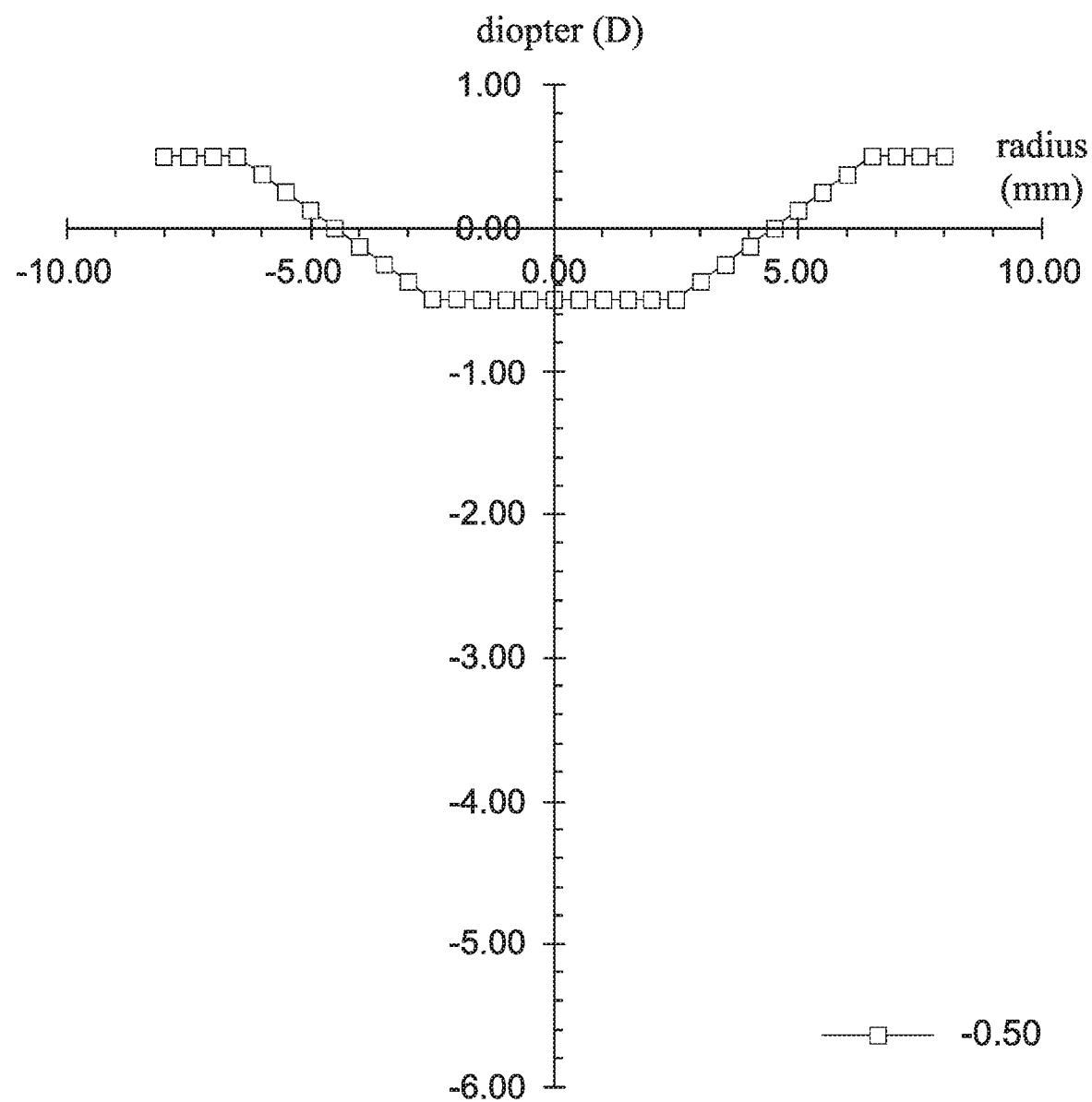
FIG. 7 shows a relationship between a radius and a diopter of a contact lens of the 2nd example.

Please refer to Table 6 and FIG. 7 simultaneously. The radius and the correspondent diopter of the contact lens of the 2nd example are listed in Table 6. FIG. 7 shows a relationship between the radius and the diopter of the contact lens of the 2nd example (the negative radius having an opposite direction with the positive radius). As shown in Table 6 and FIG. 7, the diopter of the central region is fixed, the diopter of the second annular region is different from the diopter of the central region, and the diopter of the first annular region is different from the diopter of the central region. Specifically, the diopter of the second annular region is greater than the diopter of the central region, the diopter of the second annular region increases when away from the central region, the diopter of the first annular region is greater than the diopter of the central region, and the diopter of the first annular region is fixed.

TABLE 6

| 2nd example | |
|---|---|
| radius (mm) | diopter (D) |
| −8.00 | 0.50 |
| −7.50 | 0.50 |
| −7.00 | 0.50 |
| −6.50 | 0.50 |
| −6.00 | 0.38 |
| −5.50 | 0.25 |
| −5.00 | 0.13 |
| −4.50 | 0.00 |
| −4.00 | −0.13 |
| −3.50 | −0.25 |
| −3.00 | −0.38 |
| −2.50 | −0.50 |
| −2.00 | −0.50 |
| −1.50 | −0.50 |
| −1.00 | −0.50 |
| −0.50 | −0.50 |
| 0.00 | −0.50 |
| 0.50 | −0.50 |
| 1.00 | −0.50 |
| 1.50 | −0.50 |
| 2.00 | −0.50 |
| 2.50 | −0.50 |
| 3.00 | −0.38 |
| 3.50 | −0.25 |
| 4.00 | −0.13 |
| 4.50 | 0.00 |
| 5.00 | 0.13 |
| 5.50 | 0.25 |
| 6.00 | 0.38 |
| 6.50 | 0.50 |
| 7.00 | 0.50 |
| 7.50 | 0.50 |
| 8.00 | 0.50 |

In the 2nd example, the contact lens is made of hydrogel. A composition for manufacturing the hydrogel of the 2nd example is listed in Table 7A.

TABLE 7A

| function | Ingredient | Content (wt %) |
|---|---|---|
| monomer | 2-hydroxyethyl methacrylate | 44.8 |
| monomer | glycerol monomethacrylate | 42 |
| crosslinking agent | ethylene glycol dimethacrylate | 0.6 |
| crosslinking agent | 1,1,1-trimethylol propane trimethacrylate | 0.2 |
| initiator | 2-hydroxy-2-methyl-propiophenone | 0.6 |
| diluent | glycerol | 10.35 |
| visible light absorbing agent | 1,4-bis[(2-methacryloxyethyl)amino]-9,10-anthraquinone | 0.25 |
| short-wavelength light absorbing agent | 2-(2'-hydroxy-5'-methacryloxyethylphenyl)-2H-benzotriazole | 1.2 |

In the contact lens product according to the 2nd example, a visible light absorption rate of the contact lens is Avi, a blue light absorption rate of the contact lens is Abl, an ultraviolet light absorption rate of the contact lens is Auv, and the value of Avi, Abl and Auv of the 2nd example are listed in Table 7B.

TABLE 7B

| 2nd example | | |
|---|---|---|
| Avi (%) | Abl (%) | Auv (%) |
| 25.50 | 16.50 | 75.90 |

2nd Comparative Example

The main difference between the 2nd comparative example and the 2nd example is the 2nd comparative example in lack of the visible light absorbing agent and the short-wavelength light absorbing agent. In the 2nd comparative example, the contact lens is made of hydrogel. A composition for manufacturing the hydrogel of the 2nd comparative example is listed in Table 8A.

TABLE 8A

| function | Ingredient | Content (wt %) |
|---|---|---|
| monomer | 2-hydroxyethyl methacrylate | 46.25 |
| monomer | glycerol monomethacrylate | 42 |
| crosslinking agent | ethylene glycol dimethacrylate | 0.6 |
| crosslinking agent | 1,1,1-trimethylol propane trimethacrylate | 0.2 |
| initiator | 2-hydroxy-2-methyl-propiophenone | 0.6 |
| diluent | glycerol | 10.35 |

In the contact lens product according to the 2nd comparative example, a visible light absorption rate of the contact lens is Avi, a blue light absorption rate of the contact lens is Abl, an ultraviolet light absorption rate of the contact lens is Auv, and the value of Avi, Abl and Auv of the 2nd comparative example are listed in Table 8B.

TABLE 8B

| 2nd comparative example | | |
|---|---|---|
| Avi (%) | Abl (%) | Auv(%) |
| 4.25 | 2.50 | 8.85 |

The other properties of the contact lens of the 2nd comparative example are the same as that of the 2nd example, and will not be repeated herein.

3rd Example

In the 3rd example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 3rd example can refer to FIG. 1. The structure of the contact lens of the 3rd example can refer to FIG. 4.

In the contact lens product according to the 3rd example, when a weight percentage concentration of the cycloplegic agent in the buffer solution is ConA, the following condition is satisfied: ConA=0.35%.

In the contact lens product according to the 3rd example, a diameter of the central region of the contact lens is DiC, an outer diameter of the first annular region of the contact lens is DiP1, an outer diameter of the second annular region of the contact lens is DiP2, a diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 3rd example are listed in Table 9.

TABLE 9

| | | 3rd example | |
|---|---|---|---|
| DiC (mm) | 4.00 | PowC (D) | −1.00 |
| DiP1 (mm) | 15.00 | PowP1 (D) | 0.25 |
| DiP2 (mm) | 6.00 | PowP2 (D) | −0.50 |
| DiC/DiP1 | 0.27 | |PowC − PowP1| (D) | 1.25 |
| DiC/DiP2 | 0.67 | | |

Figure 8:
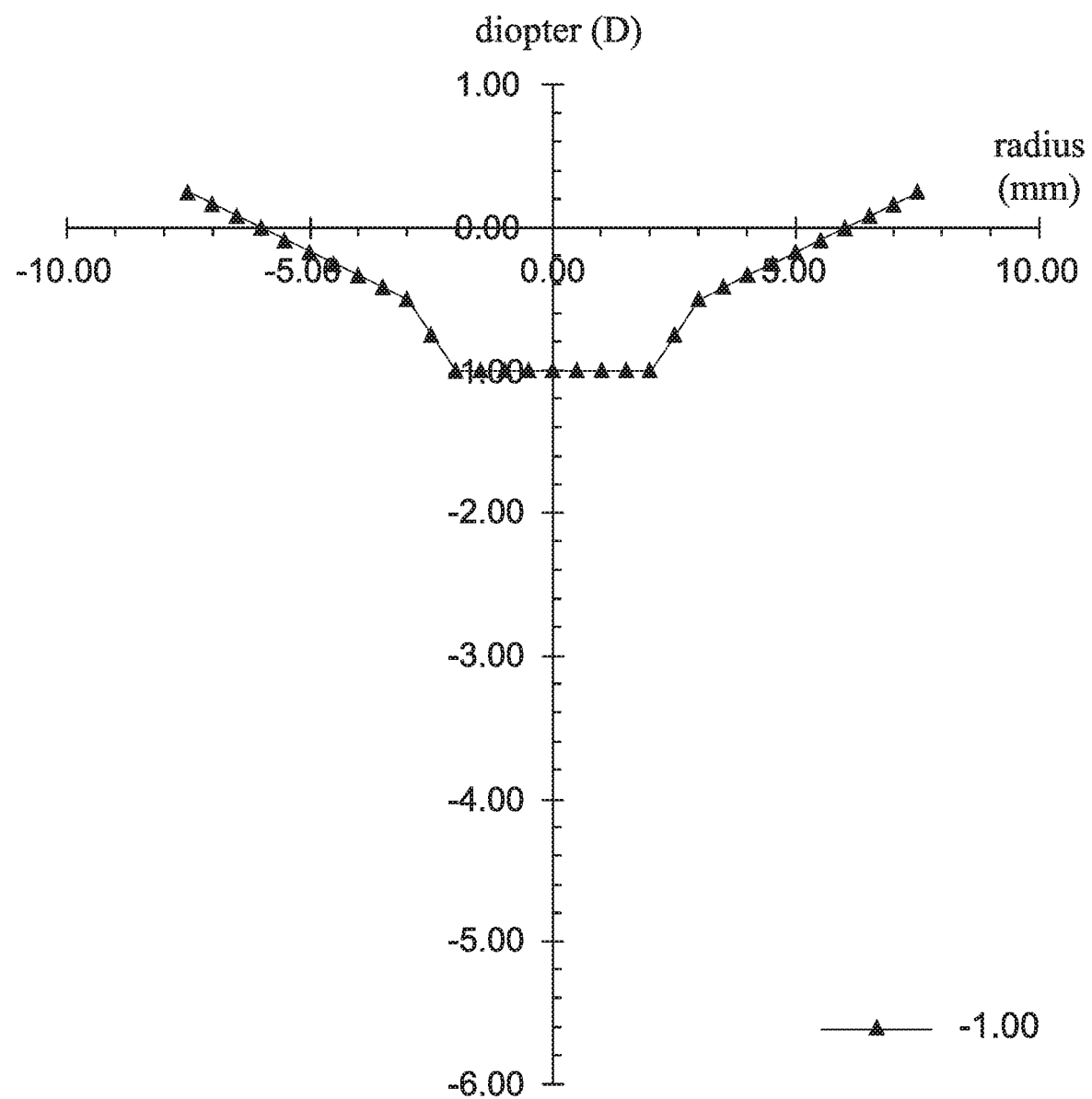
FIG. 8 shows a relationship between a radius and a diopter of a contact lens of the 3rd example.

Please refer to Table 10 and FIG. 8 simultaneously. The radius and the correspondent diopter of the contact lens of the 3rd example are listed in Table 10. FIG. 8 shows a relationship between the radius and the diopter of the contact lens of the 3rd example (the negative radius having an opposite direction with the positive radius). As shown in Table 10 and FIG. 8, the diopter of the central region is fixed, the diopter of the second annular region is different from the diopter of the central region, and the diopter of the first annular region is different from the diopter of the central region. Specifically, the diopter of the second annular region is greater than the diopter of the central region, the diopter of the second annular region increases when away from the central region, the diopter of the first annular region is greater than the diopter of the central region, and the diopter of the first annular region increases when away from the central region.

TABLE 10

| | 3rd example | | |
|---|---|---|---|
| radius (mm) | radius (mm) | radius (mm) | radius (mm) |
| −7.50 | 0.25 | 0.50 | −1.00 |
| −7.00 | 0.17 | 1.00 | −1.00 |
| −6.50 | 0.08 | 1.50 | −1.00 |
| −6.00 | 0.00 | 2.00 | −1.00 |
| −5.50 | −0.08 | 2.50 | −0.75 |
| −5.00 | −0.17 | 3.00 | −0.50 |
| −4.50 | −0.25 | 3.50 | −0.42 |
| −4.00 | −0.33 | 4.00 | −0.33 |
| −3.50 | −0.42 | 4.50 | −0.25 |
| −3.00 | −0.50 | 5.00 | −0.17 |
| −2.50 | −0.75 | 5.50 | −0.08 |
| −2.00 | −1.00 | 6.00 | 0.00 |
| −1.50 | −1.00 | 6.50 | 0.08 |
| −1.00 | −1.00 | 7.00 | 0.17 |
| −0.50 | −1.00 | 7.50 | 0.25 |
| 0.00 | −1.00 | | |

In the 3rd example, the contact lens is made of hydrogel. A composition for manufacturing the hydrogel of the 3rd example is listed in Table 11A.

TABLE 11A

| function | Ingredient | Content (wt %) |
|---|---|---|
| monomer | 2-hydroxyethyl methacrylate | 90.85 |
| monomer | N-vinyl-2-pyrrolidinone | 0.5 |
| crosslinking agent | ethylene glycol dimethacrylate | 0.6 |
| initiator | 2-hydroxy-2-methyl-propiophenone | 0.6 |
| diluent | glycerol | 6.2 |
| visible light absorbing agent | 1,4-bis[(2-methacryloxyethyl)amino]-9,10-anthraquinone | 0.25 |
| short-wavelength light absorbing agent | 2-(2'-hydroxy-5'-methacryloxyethylphenyl)-2H-benzotriazole | 1.00 |

In the contact lens product according to the 3rd example, a visible light absorption rate of the contact lens is Avi, a blue light absorption rate of the contact lens is Abl, an ultraviolet light absorption rate of the contact lens is Auv, and the value of Avi, Abl and Auv of the 3rd example are listed in Table 11B.

TABLE 11B

| 3rd example | | |
|---|---|---|
| Avi (%) | Abl (%) | Auv (%) |
| 25.50 | 16.50 | 75.90 |

3rd Comparative Example

The main difference between the 3rd comparative example and the 3rd example is the 3rd comparative example in lack of the visible light absorbing agent and the short-wavelength light absorbing agent. In the 3rd comparative example, the contact lens is made of hydrogel. A composition for manufacturing the hydrogel of the 3rd comparative example is listed in Table 12A.

TABLE 12A

| function | Ingredient | Content (wt %) |
|---|---|---|
| monomer | 2-hydroxyethyl methacrylate | 92.10 |
| monomer | N-vinyl-2-pyrrolidinone | 0.5 |
| crosslinking agent | ethylene glycol dimethacrylate | 0.6 |
| initiator | 2-hydroxy-2-methyl-propiophenone | 0.6 |
| diluent | glycerol | 6.2 |

In the contact lens product according to the 3rd comparative example, a visible light absorption rate of the contact lens is Avi, a blue light absorption rate of the contact lens is Abl, an ultraviolet light absorption rate of the contact lens is Auv, and the value of Avi, Abl and Auv of the 3rd comparative example are listed in Table 12B.

TABLE 12B

| 3rd comparative example | | |
|---|---|---|
| Avi (%) | Abl (%) | Auv (%) |
| 4.50 | 3.00 | 5.50 |

4th Example

In the 4th example, a contact lens product (not shown) includes a contact lens and a buffer solution. The contact lens is immersed in the buffer solution, and the buffer solution includes a cycloplegic agent. The contact lens includes a central region and a first annular region. The first annular region concentrically surrounds the central region. A diopter of the first annular region is different from a diopter of the central region. The schematic view of the contact lens product of the 4th example can refer to FIG. 1. The structure of the contact lens of the 4th example can refer to FIG. 3.

In the contact lens product according to the 4th example, when a weight percentage concentration of the cycloplegic agent in the buffer solution is ConA, the following condition is satisfied: ConA=0.5%.

In the contact lens product according to the 4th example, a diameter of the central region of the contact lens is DiC, an outer diameter of the first annular region of the contact lens is DiP1, the diopter of the central region of the contact lens is PowC, a maximal diopter of the first annular region of the contact lens is PowP1, and the value of DiC, DiP1, DiC/DiP1, PowC, PowP1 and |PowC−PowP1| of the 4th example are listed in Table 13.

TABLE 13

| 4th example | | | |
|---|---|---|---|
| DiC (mm) | 7.00 | PowC (D) | −1.50 |
| DiP1 (mm) | 14.00 | PowP1 (D) | −1.00 |
| DiC/DiP1 | 0.50 | |PowC − PowP1| (D) | 0.50 |

Figure 9:
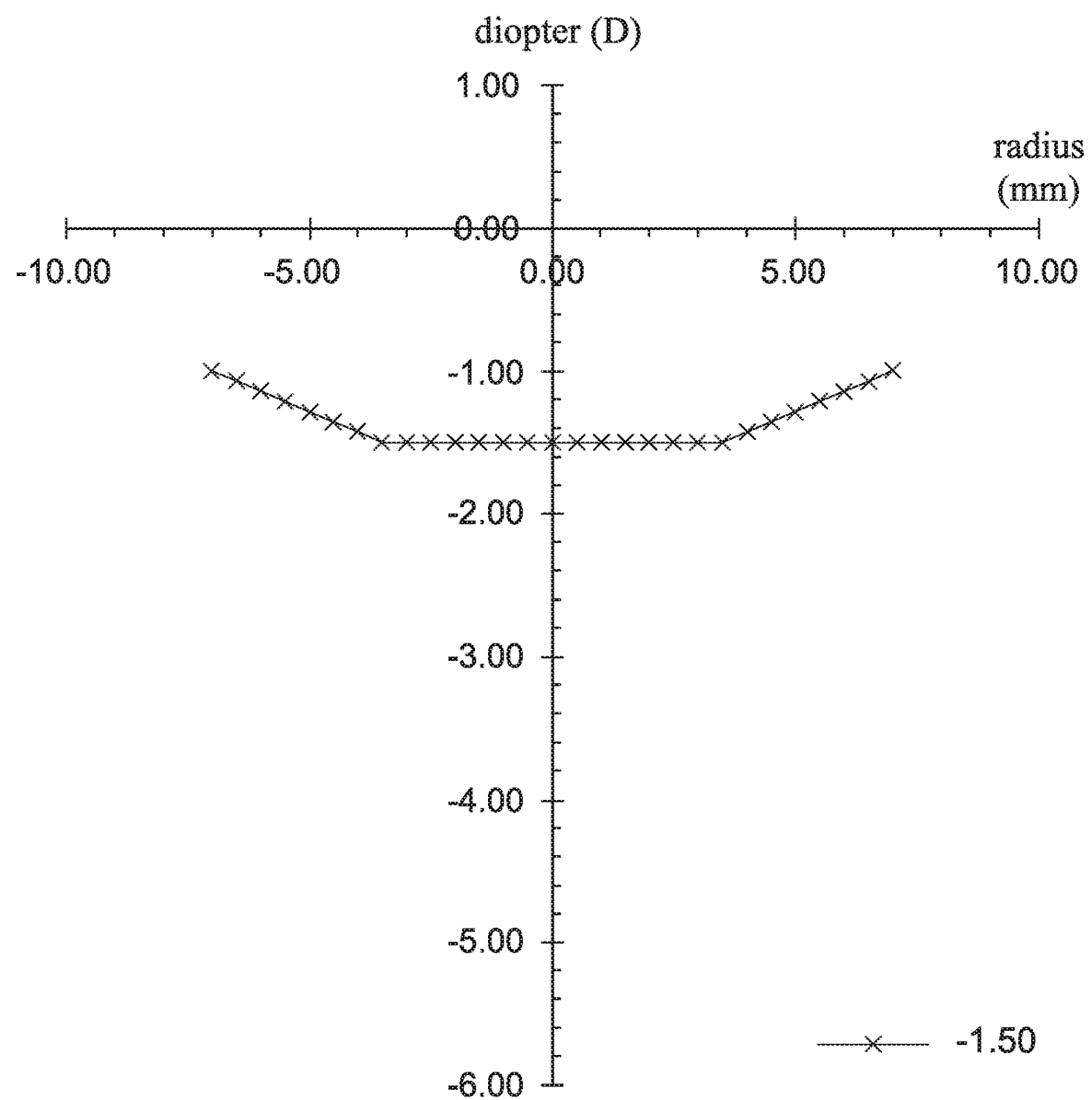
FIG. 9 shows a relationship between a radius and a diopter of a contact lens of the 4th example.

Please refer to Table 14 and FIG. 9 simultaneously. The radius and the correspondent diopter of the contact lens of the 4th example are listed in Table 14. FIG. 9 shows a relationship between the radius and the diopter of the contact lens of the 4th example (the negative radius having an opposite direction with the positive radius). As shown in Table 14 and FIG. 9, the diopter of the central region is fixed, and the diopter of the first annular region is different from the diopter of the central region. Specifically, the diopter of the first annular region is greater than the diopter of the central region, and the diopter of the first annular region increases when away from the central region.

TABLE 14

| 4th example | |
|---|---|
| radius (mm) | diopter (D) |
| −7.00 | −1.00 |
| −6.50 | −1.07 |
| −6.00 | −1.14 |
| −5.50 | −1.21 |
| −5.00 | −1.29 |
| −4.50 | −1.36 |
| −4.00 | −1.43 |
| −3.50 | −1.50 |
| −3.00 | −1.50 |
| −2.50 | −1.50 |
| −2.00 | −1.50 |
| −1.50 | −1.50 |
| −1.00 | −1.50 |
| −0.50 | −1.50 |
| 0.00 | −1.50 |
| 0.50 | −1.50 |
| 1.00 | −1.50 |
| 1.50 | −1.50 |
| 2.00 | −1.50 |
| 2.50 | −1.50 |
| 3.00 | −1.50 |
| 3.50 | −1.50 |
| 4.00 | −1.43 |
| 4.50 | −1.36 |

TABLE 14-continued

| 4th example | |
|---|---|
| radius (mm) | diopter (D) |
| 5.00 | −1.29 |
| 5.50 | −1.21 |
| 6.00 | −1.14 |
| 6.50 | −1.07 |
| 7.00 | −1.00 |

In the 4th example, the contact lens is made of hydrogel. A composition for manufacturing the hydrogel of the 4th example is listed in Table 15A.

TABLE 15A

| function | Ingredient | Content (wt %) |
|---|---|---|
| monomer | 2-hydroxyethyl methacrylate | 82 |
| monomer | methacrylic acid | 2.2 |
| crosslinking agent | ethylene glycol dimethacrylate | 0.4 |
| crosslinking agent | 1,1,1-trimethylol propane trimethacrylate | 0.2 |
| initiator | 2-hydroxy-2-methyl-propiophenone | 0.6 |
| diluent | glycerol | 13.35 |
| visible light absorbing agent | 1,4-bis[4-(2-methacryloxyethyl)phenylamino]anthraquinone | 0.25 |
| short-wavelength light absorbing agent | 2-(4-benzoyl-3-hydroxyphenoxy)ethyl acrylate | 1 |

In the contact lens product according to the 4th example, a visible light absorption rate of the contact lens is Avi, a blue light absorption rate of the contact lens is Abl, an ultraviolet light absorption rate of the contact lens is Auv, and the value of Avi, Abl and Auv of the 4th example are listed in Table 15B.

TABLE 15B

| 4th example | | |
|---|---|---|
| Avi (%) | Abl (%) | Auv(%) |
| 17.33 | 10.53 | 72.75 |

4th Comparative Example

The main difference between the 4th comparative example and the 4th example is the 4th comparative example in lack of the visible light absorbing agent and the short-wavelength light absorbing agent. In the 4th comparative example, the contact lens is made of hydrogel. A composition for manufacturing the hydrogel of the 4th comparative example is listed in Table 16A.

TABLE 16A

| function | Ingredient | Content (wt %) |
|---|---|---|
| monomer | 2-hydroxyethyl methacrylate | 83.25 |
| monomer | methacrylic acid | 2.2 |
| crosslinking agent | ethylene glycol dimethacrylate | 0.4 |
| crosslinking agent | 1,1,1-trimethylol propane trimethacrylate | 0.2 |
| initiator | 2-hydroxy-2-methyl-propiophenone | 0.6 |
| diluent | glycerol | 13.35 |

In the contact lens product according to the 4th comparative example, a visible light absorption rate of the contact lens is Avi, a blue light absorption rate of the contact lens is Abl, an ultraviolet light absorption rate of the contact lens is Auv, and the value of Avi, Abl and Auv of the 4th comparative example are listed in Table 16B.

TABLE 16B

| 4th comparative example | | |
|---|---|---|
| Avi (%) | Abl (%) | Auv (%) |
| 7.71 | 7.96 | 8.64 |

5th Example

In the 5th example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 5th example can refer to FIG. 1. The structure of the contact lens of the 5th example can refer to FIG. 4.

In the contact lens product according to the 5th example, when a weight percentage concentration of the cycloplegic agent in the buffer solution is ConA, the following condition is satisfied: ConA=0.65%.

In the contact lens product according to the 5th example, a diameter of the central region of the contact lens is DiC, an outer diameter of the first annular region of the contact lens is DiP1, an outer diameter of the second annular region of the contact lens is DiP2, a diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 5th example are listed in Table 17.

TABLE 17

| 5th example | | | |
|---|---|---|---|
| DiC (mm) | 8.00 | PowC (D) | −2.00 |
| DiP1 (mm) | 15.00 | PowP1 (D) | 0 |
| DiP2 (mm) | 11.00 | PowP2 (D) | 0 |
| DiC/DiP1 | 0.53 | |PowC − PowP1| (D) | 2.00 |
| DiC/DiP2 | 0.73 | | |

Figure 10:
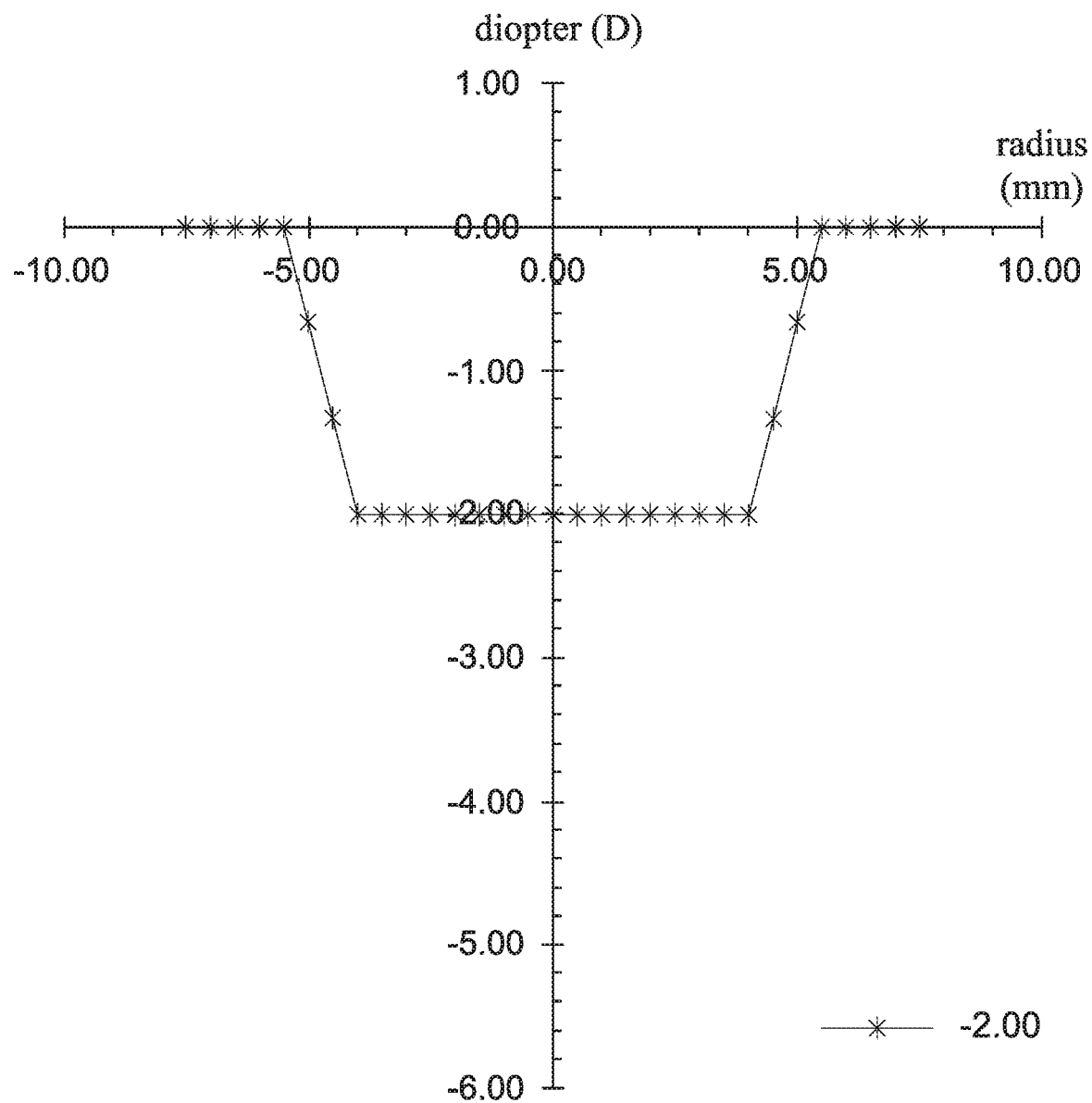
FIG. 10 shows a relationship between a radius and a diopter of a contact lens of the 5th example.

Please refer to Table 18 and FIG. 10 simultaneously. The radius and the correspondent diopter of the contact lens of the 5th example are listed in Table 18. FIG. 10 shows a relationship between the radius and the diopter of the contact lens of the 5th example (the negative radius having an opposite direction with the positive radius). As shown in Table 18 and FIG. 10, the diopter of the central region is fixed, the diopter of the second annular region is different from the diopter of the central region, and the diopter of the first annular region is different from the diopter of the central region. Specifically, the diopter of the second annular region is greater than the diopter of the central region, and the diopter of the second annular region increases when away from the central region, the diopter of the first annular region is greater than the diopter of the central region, and the diopter of the first annular region is fixed.

TABLE 18

| 5th example | |
|---|---|
| radius (mm) | radius (mm) |
| −7.50 | 0.00 |
| −7.00 | 0.00 |
| −6.50 | 0.00 |
| −6.00 | 0.00 |
| −5.50 | 0.00 |
| −5.00 | −0.67 |
| −4.50 | −1.33 |
| −4.00 | −2.00 |
| −3.50 | −2.00 |
| −3.00 | −2.00 |
| −2.50 | −2.00 |
| −2.00 | −2.00 |
| −1.50 | −2.00 |
| −1.00 | −2.00 |
| −0.50 | −2.00 |
| 0.00 | −2.00 |
| 0.50 | −2.00 |
| 1.00 | −2.00 |
| 1.50 | −2.00 |
| 2.00 | −2.00 |
| 2.50 | −2.00 |
| 3.00 | −2.00 |
| 3.50 | −2.00 |
| 4.00 | −2.00 |
| 4.50 | −1.33 |
| 5.00 | −0.67 |
| 5.50 | 0.00 |
| 6.00 | 0.00 |
| 6.50 | 0.00 |
| 7.00 | 0.00 |
| 7.50 | 0.00 |

In the 5th example, the contact lens is made of hydrogel. A composition for manufacturing the hydrogel of the 5th example is listed in Table 19A.

TABLE 19A

| function | Ingredient | Content (wt %) |
|---|---|---|
| monomer | 2-hydroxyethyl methacrylate | 45 |
| monomer | glycerol monomethacrylate | 42 |
| crosslinking agent | ethylene glycol dimethacrylate | 0.6 |
| crosslinking agent | 1,1,1-trimethylol propane trimethacrylate | 0.3 |
| initiator | 2-hydroxy-2-methyl-propiophenone | 0.6 |
| diluent | glycerol | 10.35 |
| visible light absorbing agent | 1,4-bis[(2-methacryloxyethyl)amino]-9,10-anthraquinone | 0.25 |
| short-wavelength light absorbing agent | 2-(4-benzoyl-3-hydroxyphenoxy)ethyl acrylate | 0.9 |

In the contact lens product according to the 5th example, a visible light absorption rate of the contact lens is Avi, a blue light absorption rate of the contact lens is Abl, an ultraviolet light absorption rate of the contact lens is Auv, and the value of Avi, Abl and Auv of the 5th example are listed in Table 19B.

23

TABLE 19B

| 5th example | | |
|---|---|---|
| Avi (%) | Abl (%) | Auv (%) |
| 25.50 | 16.50 | 75.90 |

5th Comparative Example

The main difference between the 5th comparative example and the 5th example is the 5th comparative example in lack of the visible light absorbing agent and the short-wavelength light absorbing agent. In the 5th comparative example, the contact lens is made of hydrogel. A composition for manufacturing the hydrogel of the 5th comparative example is listed in Table 20A.

TABLE 20A

| function | Ingredient | Content (wt %) |
|---|---|---|
| monomer | 2-hydroxyethyl methacrylate | 46.15 |
| monomer | glycerol monomethacrylate | 42 |
| crosslinking agent | ethylene glycol dimethacrylate | 0.6 |
| crosslinking agent | 1,1,1-trimethylol propane trimethacrylate | 0.3 |
| initiator | 2-hydroxy-2-methyl-propiophenone | 0.6 |
| diluent | glycerol | 10.35 |

In the contact lens product according to the 5th comparative example, a visible light absorption rate of the contact lens is Avi, a blue light absorption rate of the contact lens is Abl, an ultraviolet light absorption rate of the contact lens is Auv, and the value of Avi, Abl and Auv of the 5th comparative example are listed in Table 20B.

TABLE 20B

| 5th comparative example | | |
|---|---|---|
| Avi (%) | Abl (%) | Auv (%) |
| 5.25 | 2.25 | 7.55 |

6th Example

In the 6th example, a contact lens product (not shown) includes a contact lens and a buffer solution. The contact lens is immersed in the buffer solution, and the buffer solution includes a cycloplegic agent. The contact lens includes a central region and a first annular region. The first annular region concentrically surrounds the central region. A diopter of the first annular region is different from a diopter of the central region. The schematic view of the contact lens product of the 6th example can refer to FIG. 1. The structure of the contact lens of the 6th example can refer to FIG. 3.

In the contact lens product according to the 6th example, when a weight percentage concentration of the cycloplegic agent in the buffer solution is ConA, the following condition is satisfied: ConA=0.25%.

In the contact lens product according to the 6th example, a diameter of the central region of the contact lens is DiC, an outer diameter of the first annular region of the contact lens is DiP1, the diopter of the central region of the contact lens is PowC, a maximal diopter of the first annular region of the contact lens is PowP1, and the value of DiC, DiP1, DiC/DiP1, PowC, PowP1 and |PowC−PowP1| of the 6th example are listed in Table 21.

TABLE 21

| 6th example | | | |
|---|---|---|---|
| DiC (mm) | 9.00 | PowC (D) | −2.50 |
| DiP1 (mm) | 14.00 | PowP1 (D) | −2.25 |
| DiC/DiP1 | 0.64 | |PowC − PowP1| (D) | 0.25 |

Figure 11:
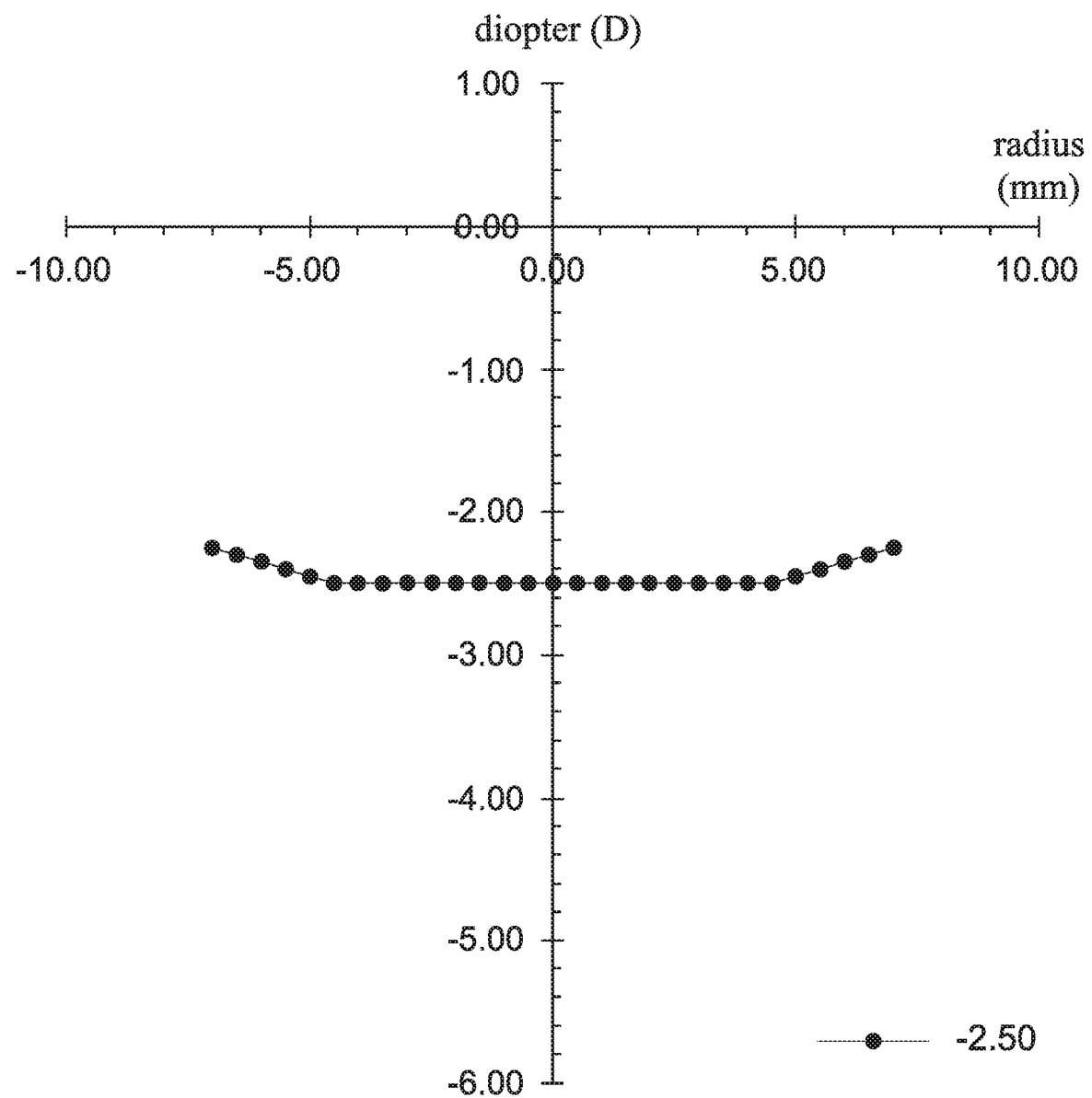
FIG. 11 shows a relationship between a radius and a diopter of a contact lens of the 6th example.

Please refer to Table 22 and FIG. 11 simultaneously. The radius and the correspondent diopter of the contact lens of the 6th example are listed in Table 22. FIG. 11 shows a relationship between the radius and the diopter of the contact lens of the 6th example (the negative radius having an opposite direction with the positive radius). As shown in Table 22 and FIG. 11, the diopter of the central region is fixed, and the diopter of the first annular region is different from the diopter of the central region. Specifically, the diopter of the first annular region is greater than the diopter of the central region, and the diopter of the first annular region increases when away from the central region.

TABLE 22

| 6th example | |
|---|---|
| radius (mm) | diopter (D) |
| −7.00 | −2.25 |
| −6.50 | −2.30 |
| −6.00 | −2.35 |
| −5.50 | −2.40 |
| −5.00 | −2.45 |
| −4.50 | −2.50 |
| −4.00 | −2.50 |
| −3.50 | −2.50 |
| −3.00 | −2.50 |
| −2.50 | −2.50 |
| −2.00 | −2.50 |
| −1.50 | −2.50 |
| −1.00 | −2.50 |
| −0.50 | −2.50 |
| 0.00 | −2.50 |
| 0.50 | −2.50 |
| 1.00 | −2.50 |
| 1.50 | −2.50 |
| 2.00 | −2.50 |
| 2.50 | −2.50 |
| 3.00 | −2.50 |
| 3.50 | −2.50 |
| 4.00 | −2.50 |
| 4.50 | −2.50 |
| 5.00 | −2.45 |
| 5.50 | −2.40 |
| 6.00 | −2.35 |
| 6.50 | −2.30 |
| 7.00 | −2.25 |

In the 6th example, the contact lens is made of hydrogel. A composition for manufacturing the hydrogel of the 6th example is listed in Table 23A.

TABLE 23A

| function | Ingredient | Content (wt %) |
|---|---|---|
| monomer | 2-hydroxyethyl methacrylate | 90.15 |
| monomer | N-vinyl-2-pyrrolidinone | 0.8 |
| crosslinking agent | ethylene glycol dimethacrylate | 0.6 |
| initiator | 2-hydroxy-2-methyl-propiophenone | 0.7 |
| diluent | glycerol | 6.3 |

TABLE 23A-continued

| function | Ingredient | Content (wt %) |
|---|---|---|
| visible light absorbing agent | 1,4-bis[(2-methacryloxyethyl)amino]-9,10-anthraquinone | 0.25 |
| short-wavelength light absorbing agent | 2-(4-benzoyl-3-hydroxyphenoxy)ethyl acrylate | 1.2 |

In the contact lens product according to the 6th example, a visible light absorption rate of the contact lens is Avi, a blue light absorption rate of the contact lens is Abl, an ultraviolet light absorption rate of the contact lens is Auv, and the value of Avi, Abl and Auv of the 6th example are listed in Table 23B.

TABLE 23B

| 6th example | | |
|---|---|---|
| Avi (%) | Abl (%) | Auv (%) |
| 24.43 | 16.50 | 75.89 |

6th Comparative Example

The main difference between the 6th comparative example and the 6th example is the 6th comparative example in lack of the visible light absorbing agent and the short-wavelength light absorbing agent. In the 6th comparative example, the contact lens is made of hydrogel. A composition for manufacturing the hydrogel of the 6th comparative example is listed in Table 24A.

TABLE 24A

| function | Ingredient | Content (wt %) |
|---|---|---|
| monomer | 2-hydroxyethyl methacrylate | 91.6 |
| monomer | N-vinyl-2-pyrrolidinone | 0.8 |
| crosslinking agent | ethylene glycol dimethacrylate | 0.6 |
| initiator | 2-hydroxy-2-methyl-propiophenone | 0.7 |
| diluent | glycerol | 6.3 |

In the contact lens product according to the 6th comparative example, a visible light absorption rate of the contact lens is Avi, a blue light absorption rate of the contact lens is Abl, an ultraviolet light absorption rate of the contact lens is Auv, and the value of Avi, Abl and Auv of the 6th comparative example are listed in Table 24B.

TABLE 24B

| 6th comparative example | | |
|---|---|---|
| Avi (%) | Abl (%) | Auv (%) |
| 8.75 | 10.88 | 15.02 |

7th Example

In the 7th example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 7th example can refer to FIG. 1. The structure of the contact lens of the 7th example can refer to FIG. 4.

In the contact lens product according to the 7th example, when a weight percentage concentration of the cycloplegic agent in the buffer solution is ConA, the following condition is satisfied: ConA=0.13%.

In the contact lens product according to the 7th example, a diameter of the central region of the contact lens is DiC, an outer diameter of the first annular region of the contact lens is DiP1, an outer diameter of the second annular region of the contact lens is DiP2, a diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 7th example are listed in Table 25.

TABLE 25

| 7th example | | | |
|---|---|---|---|
| DiC (mm) | 4.00 | PowC (D) | −3.00 |
| DiP1 (mm) | 15.00 | PowP1 (D) | −1.00 |
| DiP2 (mm) | 8.00 | PowP2 (D) | −2.00 |
| DiC/DiP1 | 0.27 | |PowC − PowP1| (D) | 2.00 |
| DiC/DiP2 | 0.50 | | |

Figure 12:
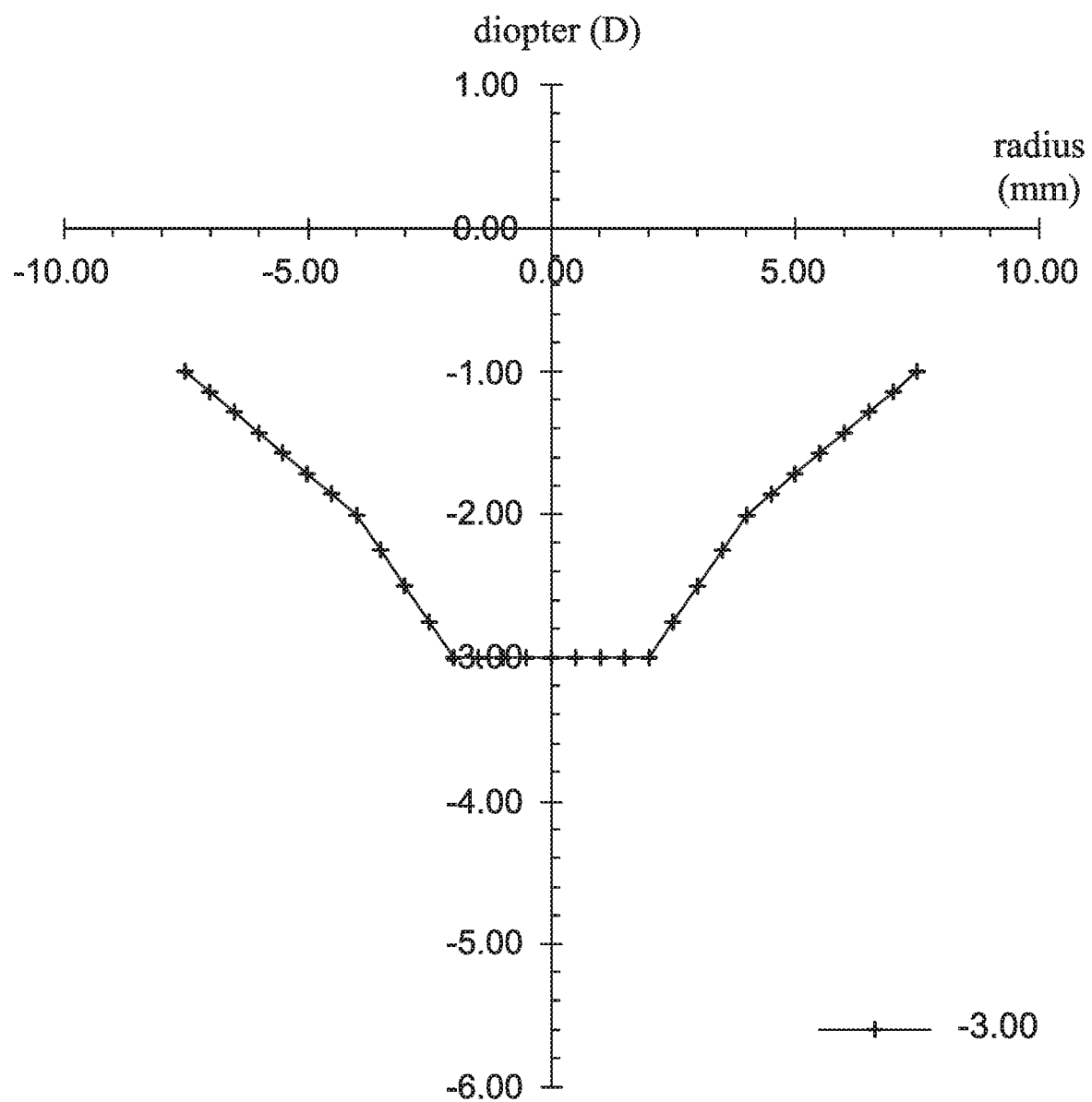
FIG. 12 shows a relationship between a radius and a diopter of a contact lens of the 7th example.

Please refer to Table 26 and FIG. 12 simultaneously. The radius and the correspondent diopter of the contact lens of the 7th example are listed in Table 26. FIG. 12 shows a relationship between the radius and the diopter of the contact lens of the 7th example (the negative radius having an opposite direction with the positive radius). As shown in Table 26 and FIG. 12, the diopter of the central region is fixed, the diopter of the second annular region is different from the diopter of the central region, and the diopter of the first annular region is different from the diopter of the central region. Specifically, the diopter of the second annular region is greater than the diopter of the central region, the diopter of the second annular region increases when away from the central region, the diopter of the first annular region is greater than the diopter of the central region, and the diopter of the first annular region increases when away from the central region.

TABLE 26

| 7th example | |
|---|---|
| radius (mm) | diopter (D) |
| −7.50 | −1.00 |
| −7.00 | −1.14 |
| −6.50 | −1.29 |
| −6.00 | −1.43 |
| −5.50 | −1.57 |
| −5.00 | −1.71 |
| −4.50 | −1.86 |
| −4.00 | −2.00 |
| −3.50 | −2.25 |
| −3.00 | −2.50 |
| −2.50 | −2.75 |
| −2.00 | −3.00 |

TABLE 26-continued

7th example

| radius (mm) | diopter (D) |
| --- | --- |
| −1.50 | −3.00 |
| −1.00 | −3.00 |
| −0.50 | −3.00 |
| 0.00 | −3.00 |
| 0.50 | −3.00 |
| 1.00 | −3.00 |
| 1.50 | −3.00 |
| 2.00 | −3.00 |
| 2.50 | −2.75 |
| 3.00 | −2.50 |
| 3.50 | −2.25 |
| 4.00 | −2.00 |
| 4.50 | −1.86 |
| 5.00 | −1.71 |
| 5.50 | −1.57 |
| 6.00 | −1.43 |
| 6.50 | −1.29 |
| 7.00 | −1.14 |
| 7.50 | −1.00 |

In the 7th example, the contact lens is made of hydrogel. A composition for manufacturing the hydrogel of the 7th example is listed in Table 27A.

TABLE 27A

| function | Ingredient | Content (wt %) |
| --- | --- | --- |
| monomer | 2-hydroxyethyl methacrylate | 81 |
| monomer | methacrylic acid | 2.3 |
| crosslinking agent | ethylene glycol dimethacrylate | 0.4 |
| crosslinking agent | 1,1,1-trimethylol propane trimethacrylate | 0.2 |
| initiator | 2-hydroxy-2-methyl-propiophenone | 0.6 |
| diluent | glycerol | 13.5 |
| short-wavelength light absorbing agent | 4-(phenyldiazenyl) phenyl methacrylate | 2.0 |

In the contact lens product according to the 7th example, a visible light absorption rate of the contact lens is Avi, a blue light absorption rate of the contact lens is Abl, an ultraviolet light absorption rate of the contact lens is Auv, and the value of Avi, Abl and Auv of the 7th example are listed in Table 27B.

TABLE 27B

7th example

| Avi (%) | Abl (%) | Auv (%) |
| --- | --- | --- |
| 22.22 | 49.81 | 96.23 |

7th Comparative Example

The main difference between the 7th comparative example and the 7th example is the 7th comparative example in lack of the short-wavelength light absorbing agent. In the 7th comparative example, the contact lens is made of hydrogel. A composition for manufacturing the hydrogel of the 7th comparative example is listed in Table 28A.

TABLE 28A

| function | Ingredient | Content (wt %) |
| --- | --- | --- |
| monomer | 2-hydroxyethyl methacrylate | 83 |
| monomer | methacrylic acid | 2.3 |
| crosslinking agent | ethylene glycol dimethacrylate | 0.4 |
| crosslinking agent | 1,1,1-trimethylol propane trimethacrylate | 0.2 |
| initiator | 2-hydroxy-2-methyl-propiophenone | 0.6 |
| diluent | glycerol | 13.5 |

In the contact lens product according to the 7th comparative example, a visible light absorption rate of the contact lens is Avi, a blue light absorption rate of the contact lens is Abl, an ultraviolet light absorption rate of the contact lens is Auv, and the value of Avi, Abl and Auv of the 7th comparative example are listed in Table 28B.

TABLE 28B

7th comparative example

| Avi (%) | Abl (%) | Auv (%) |
| --- | --- | --- |
| 7.30 | 8.21 | 13.25 |

8th Example

In the 8th example, a contact lens product (not shown) includes a contact lens and a buffer solution. The contact lens is immersed in the buffer solution, and the buffer solution includes a cycloplegic agent. The contact lens includes a central region and a first annular region. The first annular region concentrically surrounds the central region. A diopter of the first annular region is different from a diopter of the central region. The schematic view of the contact lens product of the 8th example can refer to FIG. 1. The structure of the contact lens of the 8th example can refer to FIG. 3.

In the contact lens product according to the 8th example, when a weight percentage concentration of the cycloplegic agent in the buffer solution is ConA, the following condition is satisfied: ConA=0.10%.

In the contact lens product according to the 8th example, a diameter of the central region of the contact lens is DiC, an outer diameter of the first annular region of the contact lens is DiP1, the diopter of the central region of the contact lens is PowC, a maximal diopter of the first annular region of the contact lens is PowP1, and the value of DiC, DiP1, DiC/DiP1, PowC, PowP1 and |PowC−PowP1| of the 8th example are listed in Table 29.

TABLE 29

8th example

| DiC (mm) | 5.00 | PowC (D) | −3.50 |
| --- | --- | --- | --- |
| DiP1 (mm) | 10.00 | PowP1 (D) | −1.75 |
| DiC/DiP1 | 0.50 | |PowC − PowP1| (D) | 1.75 |

Figure 13:
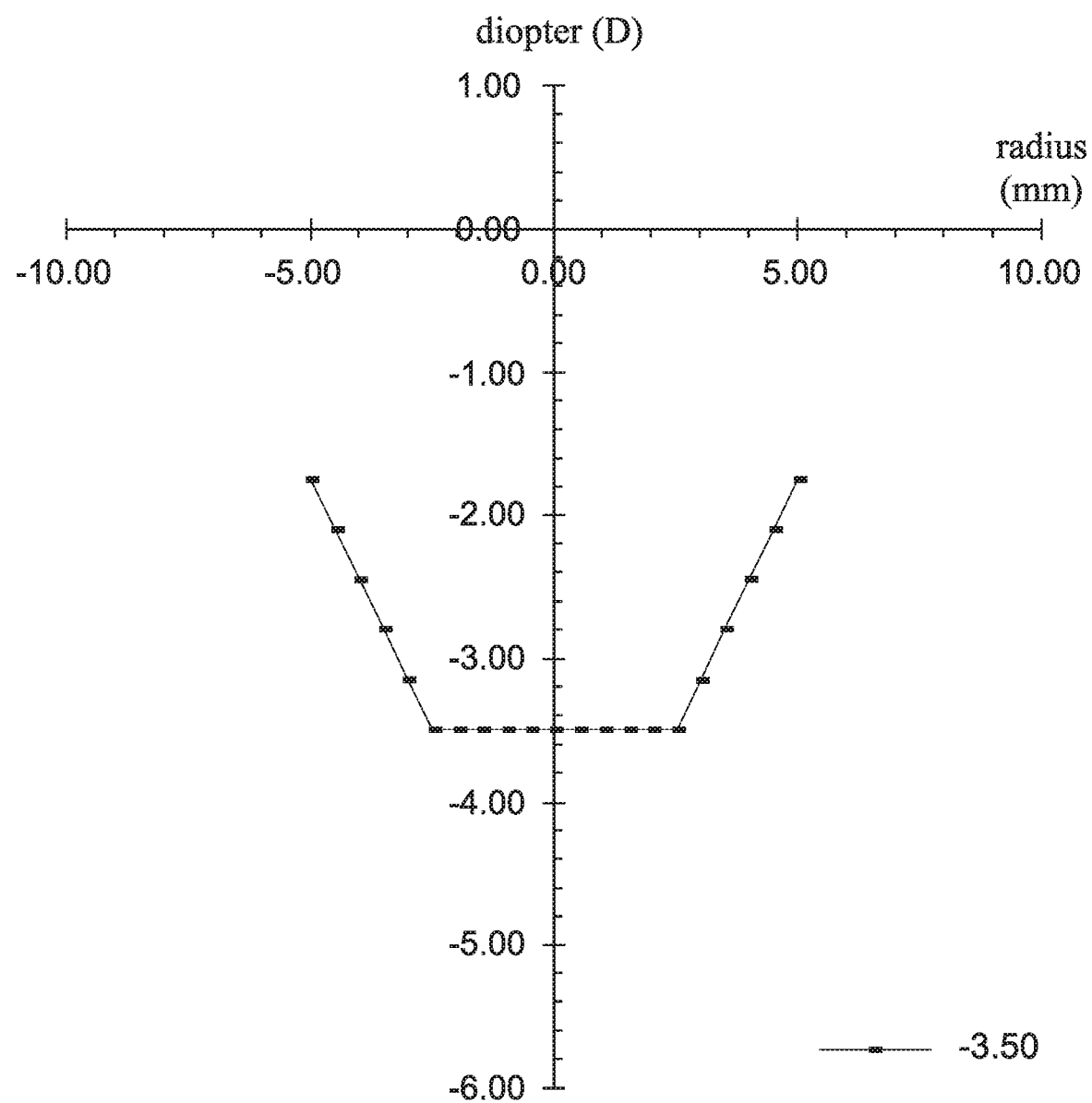
FIG. 13 shows a relationship between a radius and a diopter of a contact lens of the 8th example.

Please refer to Table 30 and FIG. 13 simultaneously. The radius and the correspondent diopter of the contact lens of the 8th example are listed in Table 30. FIG. 13 shows a relationship between the radius and the diopter of the contact lens of the 8th example (the negative radius having an opposite direction with the positive radius). As shown in Table 30 and FIG. 13, the diopter of the central region is fixed, and the diopter of the first annular region is different from the diopter of the central region. Specifically, the diopter of the first annular region is greater than the diopter of the central region, and the diopter of the first annular region increases when away from the central region.

TABLE 30

| 8th example | |
|---|---|
| radius (mm) | diopter (D) |
| −5.00 | −1.75 |
| −4.50 | −2.10 |
| −4.00 | −2.45 |
| −3.50 | −2.80 |
| −3.00 | −3.15 |
| −2.50 | −3.50 |
| −2.00 | −3.50 |
| −1.50 | −3.50 |
| −1.00 | −3.50 |
| −0.50 | −3.50 |
| 0.00 | −3.50 |
| 0.50 | −3.50 |
| 1.00 | −3.50 |
| 1.50 | −3.50 |
| 2.00 | −3.50 |
| 2.50 | −3.50 |
| 3.00 | −3.15 |
| 3.50 | −2.80 |
| 4.00 | −2.45 |
| 4.50 | −2.10 |
| 5.00 | −1.75 |

In the 8th example, the contact lens is made of hydrogel. A composition for manufacturing the hydrogel of the 8th example is listed in Table 31A.

TABLE 31A

| function | Ingredient | Content (wt %) |
|---|---|---|
| monomer | 2-hydroxyethyl methacrylate | 44 |
| monomer | glycerol monomethacrylate | 42 |
| crosslinking agent | ethylene glycol dimethacrylate | 0.5 |
| crosslinking agent | 1,1,1-trimethylol propane trimethacrylate | 0.3 |
| initiator | 2-hydroxy-2-methyl-propiophenone | 0.6 |
| diluent | glycerol | 10.6 |
| short-wavelength light absorbing agent | 4-(phenyldiazenyl) phenyl methacrylate | 2 |

In the contact lens product according to the 8th example, a visible light absorption rate of the contact lens is Avi, a blue light absorption rate of the contact lens is Abl, an ultraviolet light absorption rate of the contact lens is Auv, and the value of Avi, Abl and Auv of the 8th example are listed in Table 31B.

TABLE 31B

| 8th example | | |
|---|---|---|
| Avi (%) | Abl (%) | Auv (%) |
| 23.80 | 50.70 | 96.80 |

8th Comparative Example

The main difference between the 8th comparative example and the 8th example is the 8th comparative example in lack of the short-wavelength light absorbing agent. In the 8th comparative example, the contact lens is made of hydrogel. A composition for manufacturing the hydrogel of the 8th comparative example is listed in Table 32A.

TABLE 32A

| function | Ingredient | Content (wt %) |
|---|---|---|
| monomer | 2-hydroxyethyl methacrylate | 46 |
| monomer | glycerol monomethacrylate | 42 |
| crosslinking agent | ethylene glycol dimethacrylate | 0.5 |
| crosslinking agent | 1,1,1-trimethylol propane trimethacrylate | 0.3 |
| initiator | 2-hydroxy-2-methyl-propiophenone | 0.6 |
| diluent | glycerol | 10.6 |

In the contact lens product according to the 8th comparative example, a visible light absorption rate of the contact lens is Avi, a blue light absorption rate of the contact lens is Abl, an ultraviolet light absorption rate of the contact lens is Auv, and the value of Avi, Abl and Auv of the 8th comparative example are listed in Table 32B.

TABLE 32B

| 8th comparative example | | |
|---|---|---|
| Avi (%) | Abl (%) | Auv (%) |
| 4.25 | 2.50 | 8.85 |

9th Example

In the 9th example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 9th example can refer to FIG. 1. The structure of the contact lens of the 9th example can refer to FIG. 4.

In the contact lens product according to the 9th example, when a weight percentage concentration of the cycloplegic agent in the buffer solution is ConA, the following condition is satisfied: ConA=0.08%.

In the contact lens product according to the 9th example, a diameter of the central region of the contact lens is DiC, an outer diameter of the first annular region of the contact lens is DiP1, an outer diameter of the second annular region of the contact lens is DiP2, the diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 9th example are listed in Table 33.

TABLE 33

| 9th example | | | |
|---|---|---|---|
| DiC (mm) | 6.00 | PowC (D) | −4.00 |
| DiP1 (mm) | 14.00 | PowP1 (D) | −3.25 |
| DiP2 (mm) | 10.00 | PowP2 (D) | −3.75 |
| DiC/DiP1 | 0.43 | |PowC − PowP1| (D) | 0.75 |
| DiC/DiP2 | 0.60 | | |

Figure 14:
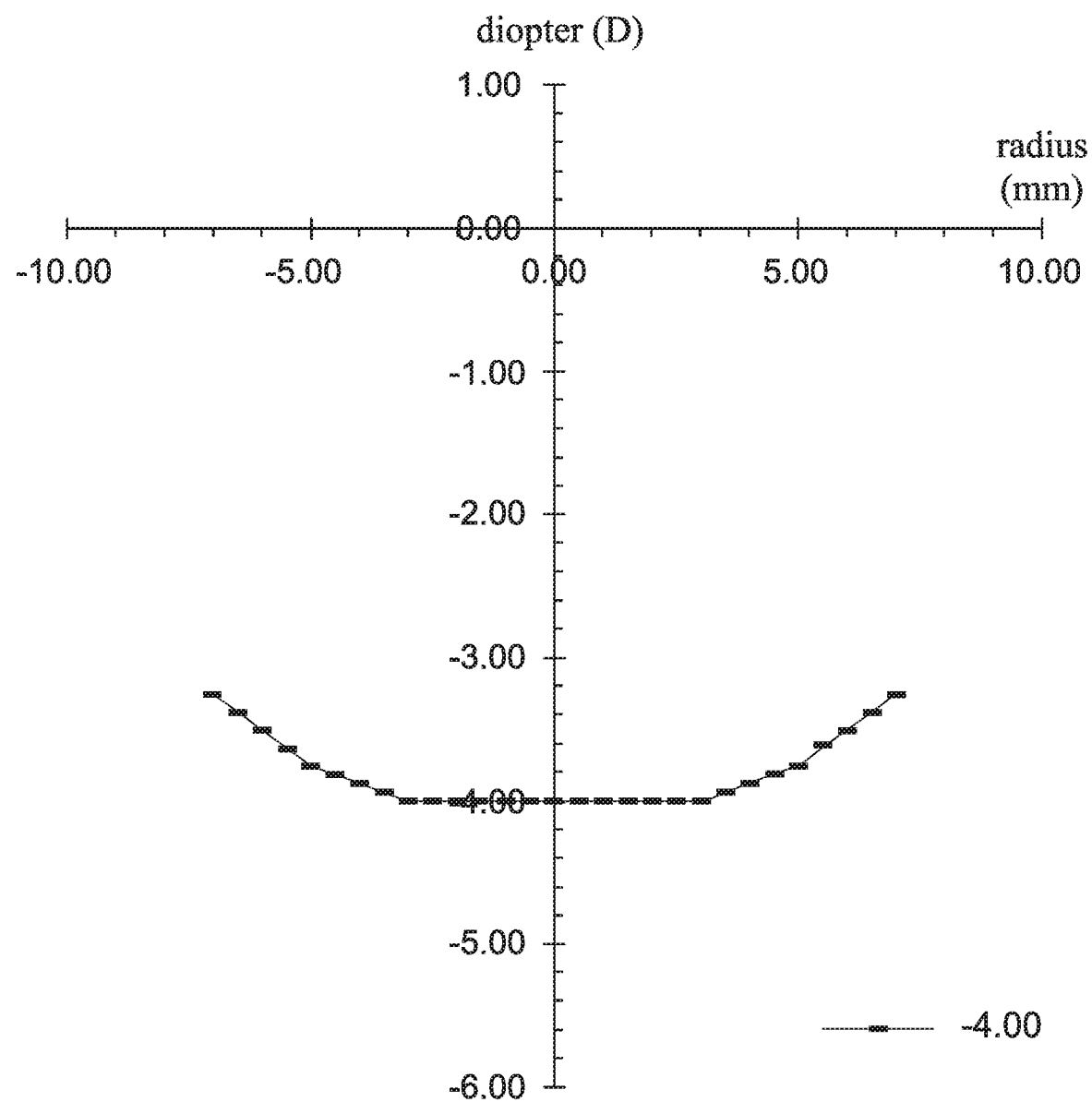
FIG. 14 shows a relationship between a radius and a diopter of a contact lens of the 9th example.

Please refer to Table 34 and FIG. 14 simultaneously. The radius and the correspondent diopter of the contact lens of the 9th example are listed in Table 34. FIG. 14 shows a relationship between the radius and the diopter of the contact lens of the 9th example (the negative radius having an opposite direction with the positive radius). As shown in Table 34 and FIG. 14, the diopter of the central region is fixed, the diopter of the second annular region is different from the diopter of the central region, and the diopter of the first annular region is different from the diopter of the central region. Specifically, the diopter of the second annular region is greater than the diopter of the central region, the diopter of the second annular region increases when away from the central region, the diopter of the first annular region is greater than the diopter of the central region, and the diopter of the first annular region increases when away from the central region.

TABLE 34

| 9th example | |
|---|---|
| radius (mm) | diopter (D) |
| −7.00 | −3.25 |
| −6.50 | −3.38 |
| −6.00 | −3.50 |
| −5.50 | −3.63 |
| −5.00 | −3.75 |
| −4.50 | −3.81 |
| −4.00 | −3.88 |
| −3.50 | −3.94 |
| −3.00 | −4.00 |
| −2.50 | −4.00 |
| −2.00 | −4.00 |
| −1.50 | −4.00 |
| −1.00 | −4.00 |
| −0.50 | −4.00 |
| 0.00 | −4.00 |
| 0.50 | −4.00 |
| 1.00 | −4.00 |
| 1.50 | −4.00 |
| 2.00 | −4.00 |
| 2.50 | −4.00 |
| 3.00 | −4.00 |
| 3.50 | −3.94 |
| 4.00 | −3.88 |
| 4.50 | −3.81 |
| 5.00 | −3.75 |
| 5.50 | −3.63 |
| 6.00 | −3.50 |
| 6.50 | −3.38 |
| 7.00 | −3.25 |

In the 9th example, the contact lens is made of hydrogel. A composition for manufacturing the hydrogel of the 9th example is listed in Table 35A.

TABLE 35A

| function | Ingredient | Content (wt %) |
|---|---|---|
| monomer | 2-hydroxyethyl methacrylate | 89.5 |
| monomer | N-vinyl-2-pyrrolidinone | 0.8 |
| crosslinking agent | ethylene glycol dimethacrylate | 0.6 |
| initiator | 2-hydroxy-2-methyl-propiophenone | 0.6 |
| diluent | glycerol | 6.5 |
| short-wavelength light absorbing agent | 4-(phenyldiazenyl) phenyl methacrylate | 2 |

In the contact lens product according to the 9th example, a visible light absorption rate of the contact lens is Avi, a blue light absorption rate of the contact lens is Abl, an ultraviolet light absorption rate of the contact lens is Auv, and the value of Avi, Abl and Auv of the 9th example are listed in Table 35B.

TABLE 35B

| 9th example | | |
|---|---|---|
| Avi (%) | Abl (%) | Auv (%) |
| 22.30 | 48.60 | 96.60 |

9th Comparative Example

The main difference between the 9th comparative example and the 9th example is the 9th comparative example in lack of the short-wavelength light absorbing agent. In the 9th comparative example, the contact lens is made of hydrogel. A composition for manufacturing the hydrogel of the 9th comparative example is listed in Table 36A.

TABLE 36A

| function | Ingredient | Content (wt %) |
|---|---|---|
| monomer | 2-hydroxyethyl methacrylate | 91.5 |
| monomer | N-vinyl-2-pyrrolidinone | 0.8 |
| crosslinking agent | ethylene glycol dimethacrylate | 0.6 |
| initiator | 2-hydroxy-2-methyl-propiophenone | 0.6 |
| diluent | glycerol | 6.5 |

In the contact lens product according to the 9th comparative example, a visible light absorption rate of the contact lens is Avi, a blue light absorption rate of the contact lens is Abl, an ultraviolet light absorption rate of the contact lens is Auv, and the value of Avi, Abl and Auv of the 9th comparative example are listed in Table 36B.

TABLE 36B

| 9th comparative example | | |
|---|---|---|
| Avi (%) | Abl (%) | Auv (%) |
| 4.50 | 3.00 | 5.50 |

10th Example

In the 10th example, a contact lens product (not shown) includes a contact lens and a buffer solution. The contact lens is immersed in the buffer solution, and the buffer solution includes a cycloplegic agent. The contact lens includes a central region and a first annular region. The first annular region concentrically surrounds the central region. A diopter of the first annular region is different from a diopter of the central region. The schematic view of the contact lens product of the 10th example can refer to FIG. 1. The structure of the contact lens of the 10th example can refer to FIG. 3.

In the contact lens product according to the 10th example, when a weight percentage concentration of the cycloplegic agent in the buffer solution is ConA, the following condition is satisfied: ConA=0.05%.

In the contact lens product according to the 10th example, a diameter of the central region of the contact lens is DiC, an outer diameter of the first annular region of the contact lens is DiP1, the diopter of the central region of the contact lens is PowC, a maximal diopter of the first annular region of the contact lens is PowP1, and the value of DiC, DiP1, DiC/DiP1, PowC, PowP1 and |PowC−PowP1| of the 10th example are listed in Table 37.

TABLE 37

| 10th example | | | |
|---|---|---|---|
| DiC (mm) | 7.00 | PowC (D) | −4.50 |
| DiP1 (mm) | 12.00 | PowP1 (D) | −3.00 |
| DiC/DiP1 | 0.58 | |PowC − PowP1| (D) | 1.50 |

Figure 15:
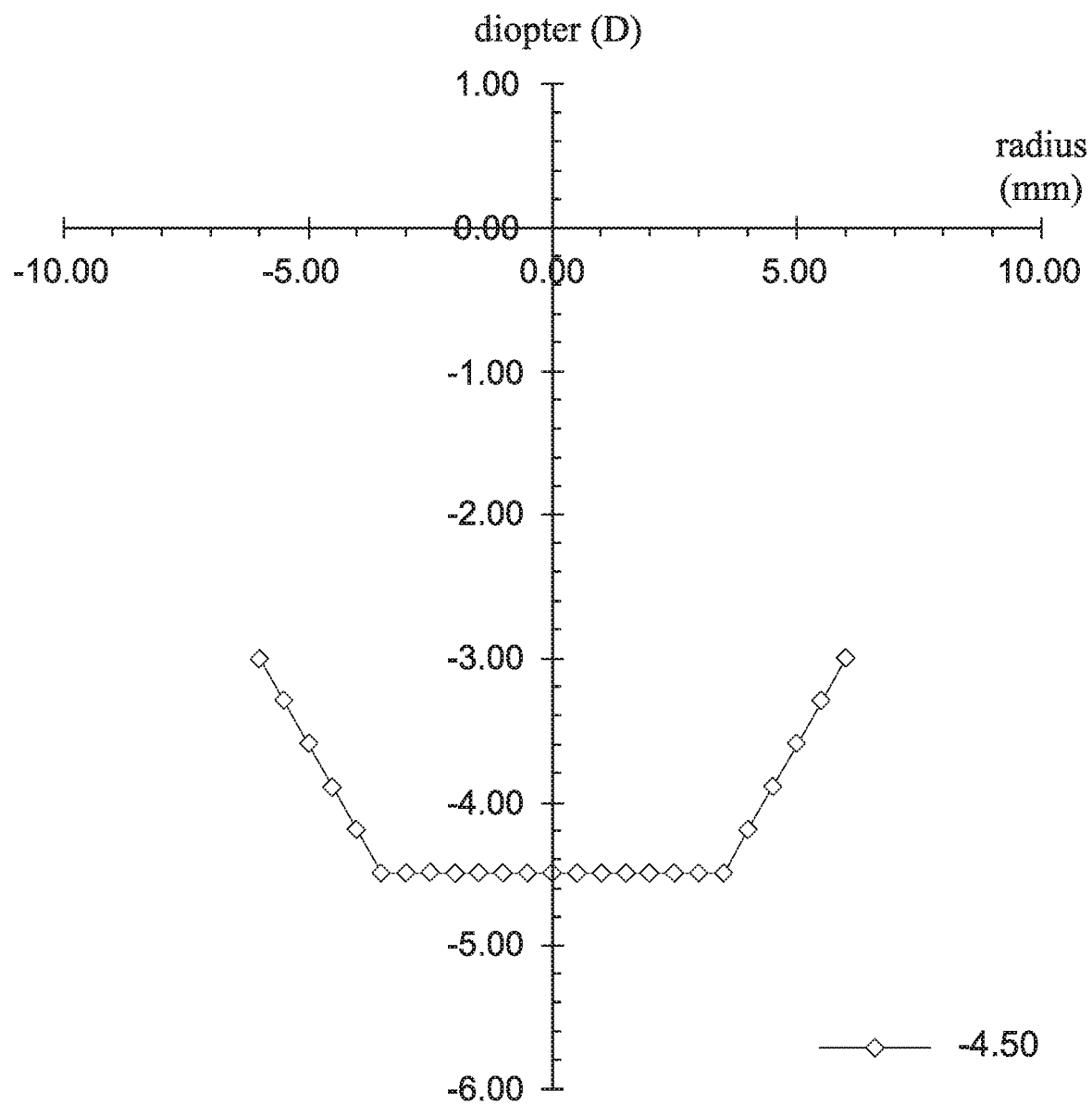
FIG. 15 shows a relationship between a radius and a diopter of a contact lens of the 10th example.

Please refer to Table 38 and FIG. 15 simultaneously. The radius and the correspondent diopter of the contact lens of the 10th example are listed in Table 38. FIG. 15 shows a relationship between the radius and the diopter of the contact lens of the 10th example (the negative radius having an opposite direction with the positive radius). As shown in Table 38 and FIG. 15, the diopter of the central region is fixed, and the diopter of the first annular region is different from the diopter of the central region. Specifically, the diopter of the first annular region is greater than the diopter of the central region, and the diopter of the first annular region increases when away from the central region.

TABLE 38

| 10th example | |
|---|---|
| radius (mm) | diopter (D) |
| −6.00 | −3.00 |
| −5.50 | −3.30 |
| −5.00 | −3.60 |
| −4.50 | −3.90 |
| −4.00 | −4.20 |
| −3.50 | −4.50 |
| −3.00 | −4.50 |
| −2.50 | −4.50 |
| −2.00 | −4.50 |
| −1.50 | −4.50 |
| −1.00 | −4.50 |
| −0.50 | −4.50 |
| 0.00 | −4.50 |
| 0.50 | −4.50 |
| 1.00 | −4.50 |
| 1.50 | −4.50 |
| 2.00 | −4.50 |
| 2.50 | −4.50 |
| 3.00 | −4.50 |
| 3.50 | −4.50 |
| 4.00 | −4.20 |
| 4.50 | −3.90 |
| 5.00 | −3.60 |

TABLE 38-continued

| 10th example | |
|---|---|
| radius (mm) | diopter (D) |
| 5.50 | −3.30 |
| 6.00 | −3.00 |

In the 10th example, the contact lens is made of silicone hydrogel. A composition for manufacturing the silicone hydrogel of the 10th example is listed in Table 39A.

TABLE 39A

| function | Ingredient | Content (wt %) |
|---|---|---|
| monomer | 2-hydroxyethyl methacrylate | 2.3 |
| monomer | 3-methacryloyloxypropyltris (trimethylsilyloxy)silane | 28 |
| monomer | N-vinyl-2-pyrrolidinone | 20.2 |
| monomer | N,N-dimethyl acrylamide | 12.3 |
| monomer | methacrylic acid | 1.5 |
| monomer | 3-(3-methacryloxy-2-hydroxypropoxy)propylbis (trimethylsiloxy)methylsilane | 21.5 |
| crosslinking agent | ethylene glycol dimethacrylate | 0.6 |
| initiator | 2-hydroxy-2-methyl-propiophenone | 0.6 |
| diluent | isopropyl alcohol | 10 |
| short-wavelength light absorbing agent | 4-(phenyldiazenyl) phenyl methacrylate | 2 |
| short-wavelength light absorbing agent | 2-(4-benzoyl-3-hydroxyphenoxy)ethyl acrylate | 1 |

In the contact lens product according to the 10th example, a visible light absorption rate of the contact lens is Avi, a blue light absorption rate of the contact lens is Abl, an ultraviolet light absorption rate of the contact lens is Auv, and the value of Avi, Abl and Auv of the 10th example are listed in Table 39B.

TABLE 39B

| 10th example | | |
|---|---|---|
| Avi (%) | Abl (%) | Auv (%) |
| 24.39 | 52.04 | 96.87 |

10th Comparative Example

The main difference between the 10th comparative example and the 10th example is the 10th comparative example in lack of the short-wavelength light absorbing agent. In the 10th comparative example, the contact lens is made of silicone hydrogel. A composition for manufacturing the silicone hydrogel of the 10th comparative example is listed in Table 40A.

TABLE 40A

| function | Ingredient | Content (wt %) |
|---|---|---|
| monomer | 2-hydroxyethyl methacrylate | 5.3 |
| monomer | 3-methacryloyloxypropyltris (trimethylsilyloxy)silane | 28 |
| monomer | N-vinyl-2-pyrrolidinone | 20.2 |
| monomer | N,N-dimethyl acrylamide | 12.3 |

TABLE 40A-continued

| function | Ingredient | Content (wt %) |
|---|---|---|
| monomer | methacrylic acid | 1.5 |
| monomer | 3-(3-methacryloxy-2-hydroxypropoxy)propylbis(trimethylsiloxy)methylsilane | 21.5 |
| crosslinking agent | ethylene glycol dimethacrylate | 0.6 |
| initiator | 2-hydroxy-2-methyl-propiophenone | 0.6 |
| diluent | isopropyl alcohol | 10 |

In the contact lens product according to the 10th comparative example, a visible light absorption rate of the contact lens is Avi, a blue light absorption rate of the contact lens is Abl, an ultraviolet light absorption rate of the contact lens is Auv, and the value of Avi, Abl and Auv of the 10th comparative example are listed in Table 40B.

TABLE 40B

| 10th comparative example | | |
|---|---|---|
| Avi (%) | Abl (%) | Auv (%) |
| 7.85 | 10.31 | 19.51 |

11th Example

In the 11th example, a contact lens product (not shown) includes a contact lens and a buffer solution. The contact lens is immersed in the buffer solution, and the buffer solution includes a cycloplegic agent. The contact lens includes a central region, a first annular region and a second annular region. The central region, the second annular region and the first annular region are sequentially connected from a center of the contact lens to a periphery of the contact lens and are concentric. At least one of the central region, the second annular region and the first annular region is aspheric. The schematic view of the contact lens product of the 11th example can refer to FIG. 1. The structure of the contact lens of the 11th example can refer to FIG. 4.

In the contact lens product according to the 11th example, when a weight percentage concentration of the cycloplegic agent in the buffer solution is ConA, the following condition is satisfied: ConA=0.03%.

In the contact lens product according to the 11th example, a diameter of the central region of the contact lens is DiC, an outer diameter of the first annular region of the contact lens is DiP1, an outer diameter of the second annular region of the contact lens is DiP2, a diopter of the central region of the contact lens is PowC, a maximal diopter of the first annular region of the contact lens is PowP1, a maximal diopter of the second annular region of the contact lens is PowP2, and the value of DiC, DiP1, DiP2, DiC/DiP1, DiC/DiP2, PowC, PowP1, PowP2 and |PowC−PowP1| of the 11th example are listed in Table 41.

TABLE 41

| 11th example | | | |
|---|---|---|---|
| DiC (mm) | 8.00 | PowC (D) | −5.00 |
| DiP1 (mm) | 13.00 | PowP1 (D) | −2.75 |
| DiP2 (mm) | 10.00 | PowP2 (D) | −4.00 |
| DiC/DiP1 | 0.62 | |PowC − PowP1| (D) | 2.25 |
| DiC/DiP2 | 0.80 | | |

Figure 16:
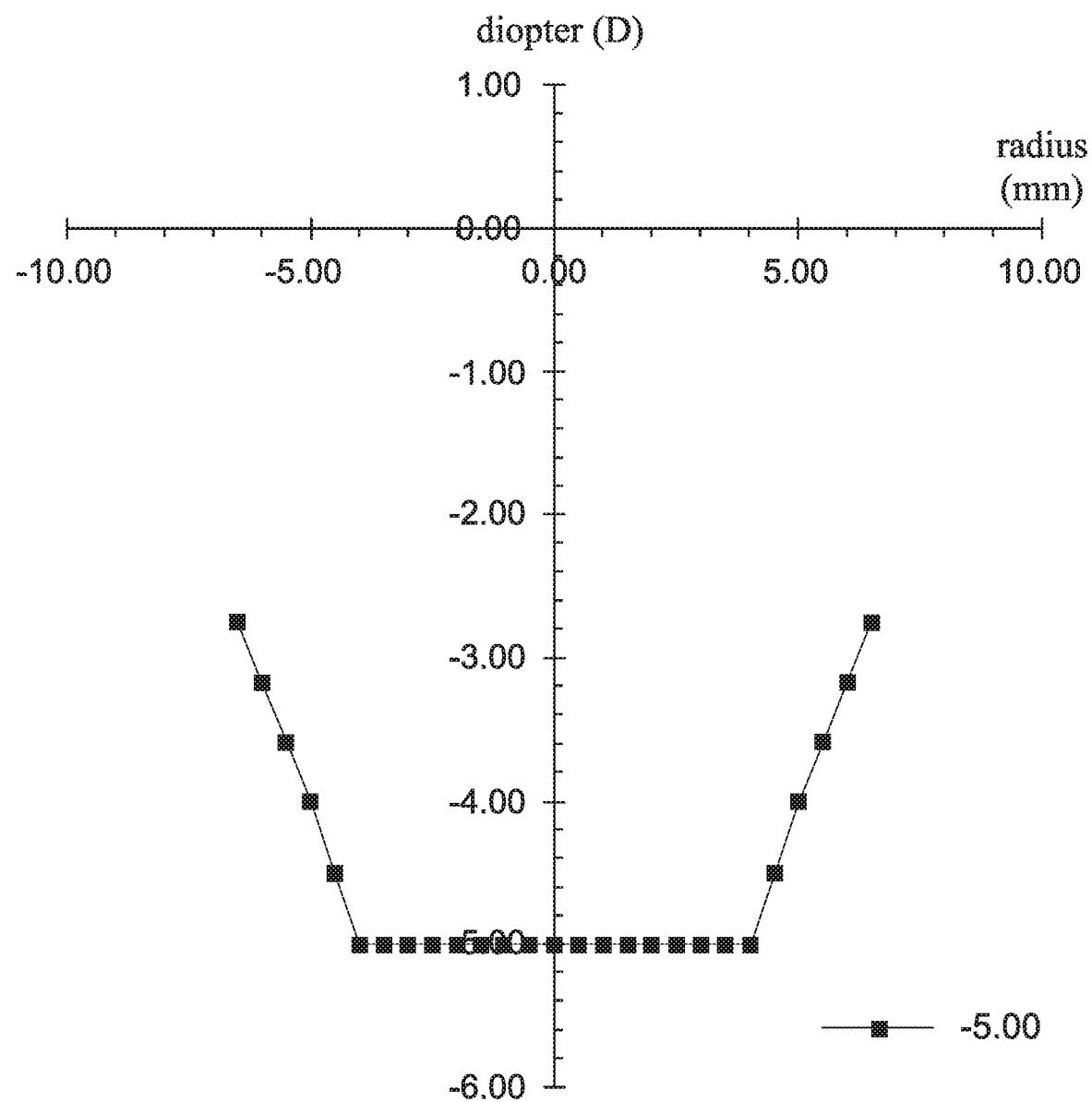
FIG. 16 shows a relationship between a radius and a diopter of a contact lens of the 11th example.

Please refer to Table 42 and FIG. 16 simultaneously. The radius and the correspondent diopter of the contact lens of the 11th example are listed in Table 42. FIG. 16 shows a relationship between the radius and the diopter of the contact lens of the 11th example (the negative radius having an opposite direction with the positive radius). As shown in Table 42 and FIG. 16, the diopter of the central region is fixed, the diopter of the second annular region is different from the diopter of the central region, and the diopter of the first annular region is different from the diopter of the central region. Specifically, the diopter of the second annular region is greater than the diopter of the central region, the diopter of the second annular region increases when away from the central region, the diopter of the first annular region is greater than the diopter of the central region, and the diopter of the first annular region increases when away from the central region.

TABLE 42

| 11th example | |
|---|---|
| radius (mm) | diopter (D) |
| −6.50 | −2.75 |
| −6.00 | −3.17 |
| −5.50 | −3.58 |
| −5.00 | −4.00 |
| −4.50 | −4.50 |
| −4.00 | −5.00 |
| −3.50 | −5.00 |
| −3.00 | −5.00 |
| −2.50 | −5.00 |
| −2.00 | −5.00 |
| −1.50 | −5.00 |
| −1.00 | −5.00 |
| −0.50 | −5.00 |
| 0.00 | −5.00 |
| 0.50 | −5.00 |
| 1.00 | −5.00 |
| 1.50 | −5.00 |
| 2.00 | −5.00 |
| 2.50 | −5.00 |
| 3.00 | −5.00 |
| 3.50 | −5.00 |
| 4.00 | −5.00 |
| 4.50 | −4.50 |
| 5.00 | −4.00 |
| 5.50 | −3.58 |
| 6.00 | −3.17 |
| 6.50 | −2.75 |

In the 11th example, the contact lens is made of silicone hydrogel. A composition for manufacturing the silicone hydrogel of the 11th example is listed in Table 43A.

TABLE 43A

| function | Ingredient | Content (wt %) |
|---|---|---|
| monomer | 2-hydroxyethyl methacrylate | 4 |
| monomer | 3-methacryloyloxypropyltris(trimethylsilyloxy)silane | 28 |
| monomer | N-vinyl-2-pyrrolidinone | 20.5 |
| monomer | N,N-dimethyl acrylamide | 12.3 |
| monomer | (3-acryloxy-2-hydroxypropoxypropyl)terminated polydimethylsiloxane | 22 |
| crosslinking agent | ethylene glycol dimethacrylate | 0.5 |
| initiator | 2-hydroxy-2-methyl-propiophenone | 0.6 |
| diluent | 1-hexanol | 11 |
| short-wavelength light absorbing agent | 2-(4-benzoyl-3-hydroxyphenoxy)ethyl acrylate | 1.1 |

In the contact lens product according to the 11th example, a visible light absorption rate of the contact lens is Avi, a blue light absorption rate of the contact lens is Abl, an ultraviolet light absorption rate of the contact lens is Auv, and the value of Avi, Abl and Auv of the 11th example are listed in Table 43B.

TABLE 43B

| 11th example | | |
|---|---|---|
| Avi (%) | Abl (%) | Auv (%) |
| 9.00 | 14.90 | 90.00 |

11th Comparative Example

The main difference between the 11th comparative example and the 11th example is the 11th comparative example in lack of the short-wavelength light absorbing agent. In the 11th comparative example, the contact lens is made of silicone hydrogel. A composition for manufacturing the silicone hydrogel of the 11th comparative example is listed in Table 44A.

TABLE 44A

| function | Ingredient | Content (wt %) |
|---|---|---|
| monomer | 2-hydroxyethyl methacrylate | 5.1 |
| monomer | 3-methacryloyloxypropyltris (trimethylsilyloxy)silane | 28 |
| monomer | N-vinyl-2-pyrrolidinone | 20.5 |
| monomer | N,N-dimethyl acrylamide | 12.3 |
| monomer | (3-acryloxy-2-hydroxypropoxypropyl)terminated polydimethylsiloxane | 22 |
| crosslinking agent | ethylene glycol dimethacrylate | 0.5 |
| initiator | 2-hydroxy-2-methyl-propiophenone | 0.6 |
| diluent | 1-hexanol | 11 |

In the contact lens product according to the 11th comparative example, a visible light absorption rate of the contact lens is Avi, a blue light absorption rate of the contact lens is Abl, an ultraviolet light absorption rate of the contact lens is Auv, and the value of Avi, Abl and Auv of the 11th comparative example are listed in Table 44B.

TABLE 44B

| 11th comparative example | | |
|---|---|---|
| Avi (%) | Abl (%) | Auv (%) |
| 7.80 | 9.40 | 24.00 |

12th Example

In the 12th example, a contact lens product (not shown) includes a contact lens and a buffer solution. The contact lens is immersed in the buffer solution, and the buffer solution includes a cycloplegic agent. The contact lens includes a central region, a first annular region, a second annular region and a third annular region. The central region, the third annular region, the second annular region and the first annular region are sequentially connected from a center of the contact lens to a periphery of the contact lens and are concentric. At least one of the central region, the third annular region, the second annular region and the first annular region is aspheric. The schematic view of the contact lens product of the 12th example can refer to FIG. 1. The structure of the contact lens of the 12th example can refer to FIG. 5.

In the contact lens product according to the 12th example, when a weight percentage concentration of the cycloplegic agent in the buffer solution is ConA, the following condition is satisfied: ConA=0.01%.

In the contact lens product according to the 12th example, a diameter of the central region of the contact lens is DiC, an outer diameter of the first annular region of the contact lens is DiP1, an outer diameter of the second annular region of the contact lens is DiP2, an outer diameter of the third annular region of the contact lens is DiP3, a diopter of the central region of the contact lens is PowC, a maximal diopter of the first annular region of the contact lens is PowP1, a maximal diopter of the second annular region of the contact lens is PowP2, a maximal diopter of the third annular region of the contact lens is PowP3, and the value of DiC, DiP1, DiP2, DiP3, DiC/DiP1, DiC/DiP2, PowC, PowP1, PowP2, PowP3 and |PowC−PowP1| of the 12th example are listed in Table 45.

TABLE 45

| 12th example | | | |
|---|---|---|---|
| DiC (mm) | 4.00 | PowC (D) | −5.50 |
| DiP1 (mm) | 16.00 | PowP1 (D) | −3.00 |
| DiP2 (mm) | 12.00 | PowP2 (D) | −3.00 |
| DiP3 (mm) | 8.00 | PowP3 (D) | −3.75 |
| DiC/DiP1 | 0.25 | |PowC − PowP1| (D) | 2.50 |
| DiC/DiP2 | 0.33 | | |

Figure 17:
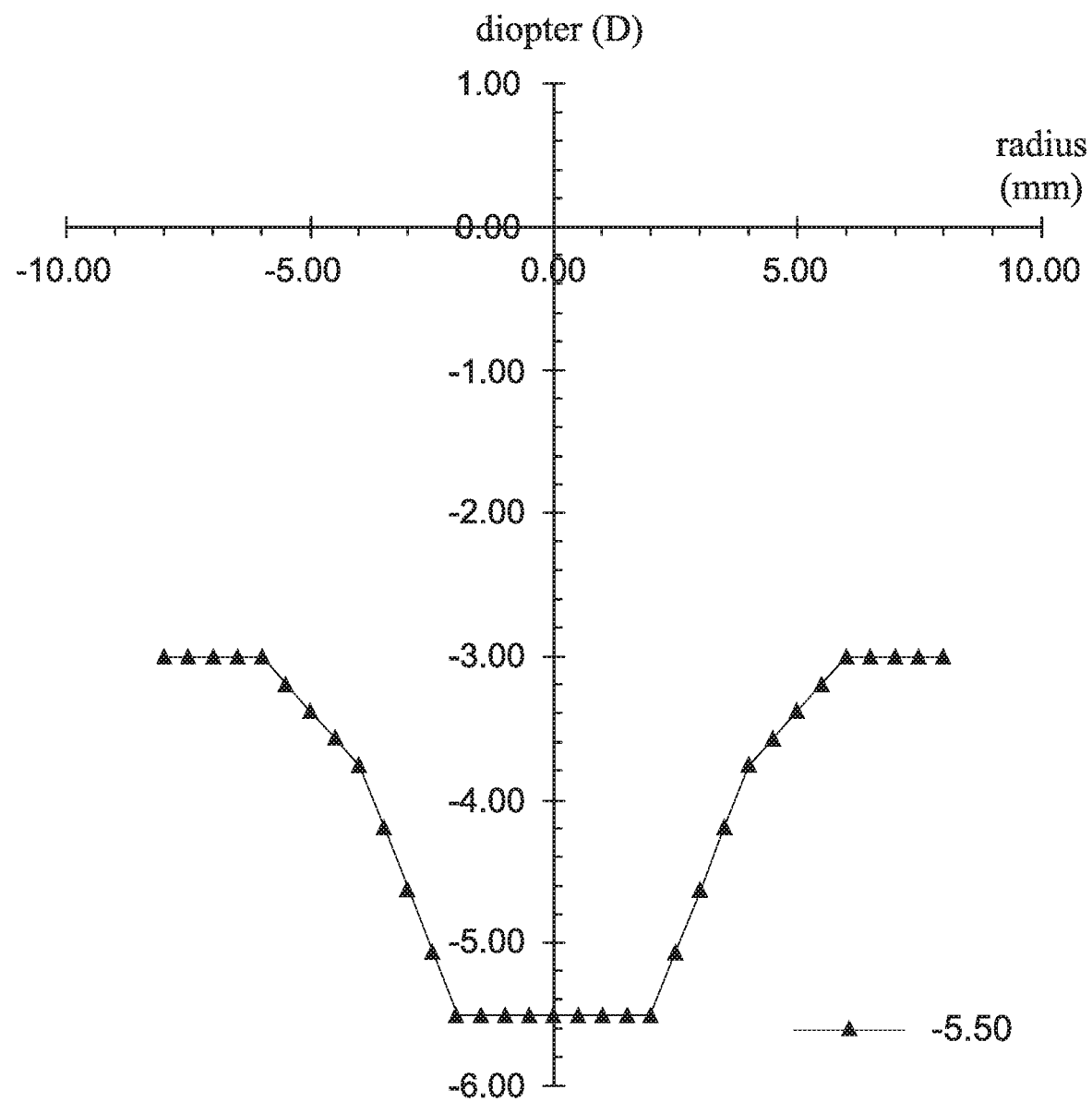
FIG. 17 shows a relationship between a radius and a diopter of a contact lens of the 12th example.

Please refer to Table 46 and FIG. 17 simultaneously. The radius and the correspondent diopter of the contact lens of the 12th example are listed in Table 46. FIG. 17 shows a relationship between the radius and the diopter of the contact lens of the 12th example (the negative radius having an opposite direction with the positive radius). As shown in Table 46 and FIG. 17, the diopter of the central region is fixed, the diopter of the third annular region is different from the diopter of the central region, the diopter of the second annular region is different from the diopter of the central region, and the diopter of the first annular region is different from the diopter of the central region. Specifically, the diopter of the third annular region is greater than the diopter of the central region, the diopter of the third annular region increases when away from the central region, the diopter of the second annular region is greater than the diopter of the central region, the diopter of the second annular region increases when away from the central region, the diopter of the first annular region is greater than the diopter of the central region, and the diopter of the first annular region is fixed.

TABLE 46

| 12th example | |
|---|---|
| radius (mm) | diopter (D) |
| −8.00 | −3.00 |
| −7.50 | −3.00 |
| −7.00 | −3.00 |
| −6.50 | −3.00 |
| −6.00 | −3.00 |
| −5.50 | −3.19 |

TABLE 46-continued

| 12th example | |
|---|---|
| radius (mm) | diopter (D) |
| −5.00 | −3.38 |
| −4.50 | −3.56 |
| −4.00 | −3.75 |
| −3.50 | −4.19 |
| −3.00 | −4.63 |
| −2.50 | −5.06 |
| −2.00 | −5.50 |
| −1.50 | −5.50 |
| −1.00 | −5.50 |
| −0.50 | −5.50 |
| 0.00 | −5.50 |
| 0.50 | −5.50 |
| 1.00 | −5.50 |
| 1.50 | −5.50 |
| 2.00 | −5.50 |
| 2.50 | −5.06 |
| 3.00 | −4.63 |
| 3.50 | −4.19 |
| 4.00 | −3.75 |
| 4.50 | −3.56 |
| 5.00 | −3.38 |
| 5.50 | −3.19 |
| 6.00 | −3.00 |
| 6.50 | −3.00 |
| 7.00 | −3.00 |
| 7.50 | −3.00 |
| 8.00 | −3.00 |

In the 12th example, the contact lens is made of silicone hydrogel. A composition for manufacturing the silicone hydrogel of the 12th example is listed in Table 47A.

TABLE 47A

| function | Ingredient | Content (wt %) |
|---|---|---|
| monomer | 2-hydroxyethyl methacrylate | 4.2 |
| monomer | 3-methacryloyloxypropyltris (trimethylsilyloxy)silane | 24.1 |
| monomer | N-vinyl-2-pyrrolidinone | 19.99 |
| monomer | N,N-dimethyl acrylamide | 11.00 |
| monomer | methyl methacrylate | 4.2 |
| oligomer | polysiloxane macromer | 25 |
| initiator | 2-hydroxy-2-methyl-propiophenone | 0.6 |
| diluent | ethanol | 10 |
| visible light absorbing agent | 1,4-bis[(2-methacryloxyethyl)amino]-9,10-anthraquinone | 0.01 |
| short-wavelength light absorbing agent | 2-(4-benzoyl-3-hydroxyphenoxy)ethyl acrylate | 0.9 |

In the contact lens product according to the 12th example, a visible light absorption rate of the contact lens is Avi, a blue light absorption rate of the contact lens is Abl, an ultraviolet light absorption rate of the contact lens is Auv, and the value of Avi, Abl and Auv of the 12th example are listed in Table 47B.

TABLE 47B

| 12th example | | |
|---|---|---|
| Avi (%) | Abl (%) | Auv (%) |
| 9.70 | 12.40 | 89.20 |

12th Comparative Example

The main difference between the 12th comparative example and the 12th example is the 12th comparative example in lack of the visible light absorbing agent and the short-wavelength light absorbing agent. In the 12th comparative example, the contact lens is made of silicone hydrogel. A composition for manufacturing the silicone hydrogel of the 12th comparative example is listed in Table 48A.

TABLE 48A

| function | Ingredient | Content (wt %) |
|---|---|---|
| monomer | 2-hydroxyethyl methacrylate | 5.11 |
| monomer | 3-methacryloyloxypropyltris (trimethylsilyloxy)silane | 24.1 |
| monomer | N-vinyl-2-pyrrolidinone | 19.99 |
| monomer | N,N-dimethyl acrylamide | 11.00 |
| monomer | methyl methacrylate | 4.2 |
| oligomer | polysiloxane macromer | 25 |
| initiator | 2-hydroxy-2-methyl-propiophenone | 0.6 |
| diluent | ethanol | 10 |

In the contact lens product according to the 12th comparative example, a visible light absorption rate of the contact lens is Avi, a blue light absorption rate of the contact lens is Abl, an ultraviolet light absorption rate of the contact lens is Auv, and the value of Avi, Abl and Auv of the 12th comparative example are listed in Table 48B.

TABLE 48B

| 12th comparative example | | |
|---|---|---|
| Avi (%) | Abl (%) | Auv (%) |
| 6.37 | 7.40 | 24.20 |

13th Example

In the 13th example, a contact lens product (not shown) includes a contact lens and a buffer solution. The contact lens is immersed in the buffer solution, and the buffer solution includes a cycloplegic agent. The schematic view of the contact lens product of the 13th example can refer to FIG. 1. The structure of the contact lens of the 13th example can refer to FIG. 2.

In the contact lens product according to the 13th example, when a weight percentage concentration of the cycloplegic agent in the buffer solution is ConA, the following condition is satisfied: ConA=0.18%.

In the contact lens product according to the 13th example, a diameter of the contact lens is 5 mm, a diopter of the contact lens is −3.50D.

Figure 18:
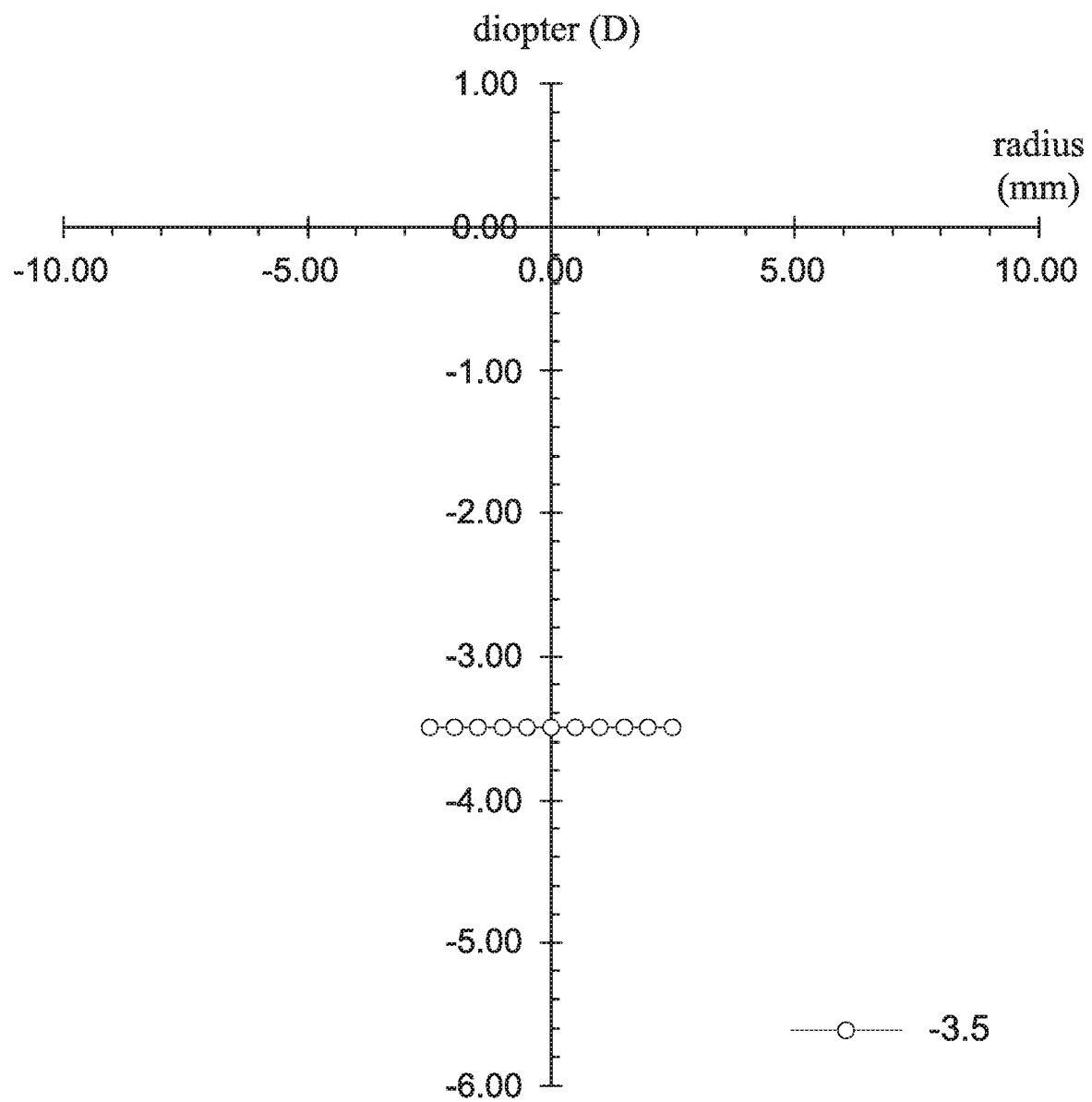
FIG. 18 shows a relationship between a radius and a diopter of a contact lens of the 13th example.

Please refer to Table 49 and FIG. 18 simultaneously. The radius and the correspondent diopter of the contact lens of the 13th example are listed in Table 49. FIG. 18 shows a relationship between the radius and the diopter of the contact lens of the 13th example (the negative radius having an opposite direction with the positive radius). As shown in Table 49 and FIG. 18, the diopter of the contact lens is fixed.

TABLE 49

| 13th example | |
|---|---|
| radius (mm) | diopter (D) |
| −2.50 | −3.50 |
| −2.00 | −3.50 |

TABLE 49-continued

13th example

| radius (mm) | diopter (D) |
| --- | --- |
| −1.50 | −3.50 |
| −1.00 | −3.50 |
| −0.50 | −3.50 |
| 0.00 | −3.50 |
| 0.50 | −3.50 |
| 1.00 | −3.50 |
| 1.50 | −3.50 |
| 2.00 | −3.50 |
| 2.50 | −3.50 |

In the 13th example, the contact lens is made of silicone hydrogel. A composition for manufacturing the silicone hydrogel of the 13th example is listed in Table 50A.

TABLE 50A

| function | Ingredient | Content (wt %) |
| --- | --- | --- |
| monomer | 2-hydroxyethyl methacrylate | 3.5 |
| monomer | 3-methacryloyloxypropyltris (trimethylsilyloxy)silane | 26.00 |
| monomer | N-vinyl-2-pyrrolidinone | 19.50 |
| monomer | N,N-dimethyl acrylamide | 11.10 |
| monomer | methyl methacrylate | 4.10 |
| oligomer | polysiloxane macromer | 24.50 |
| initiator | 2-hydroxy-2-methyl-propiophenone | 1.00 |
| diluent | ethanol | 9.00 |
| visible light absorbing agent | 1,4-bis[(2-methacryloxyethyl)amino]-9,10-anthraquinone | 0.30 |
| short-wavelength light absorbing agent | 2-(4-benzoyl-3-hydroxyphenoxy)ethyl acrylate | 1.00 |

In the contact lens product according to the 13th example, a visible light absorption rate of the contact lens is Avi, a blue light absorption rate of the contact lens is Abl, an ultraviolet light absorption rate of the contact lens is Auv, and the value of Avi, Abl and Auv of the 13th example are listed in Table 50B.

TABLE 50B

13th example

| Avi (%) | Abl (%) | Auv (%) |
| --- | --- | --- |
| 29.30 | 24.70 | 89.70 |

13th Comparative Example

The main difference between the 13th comparative example and the 13th example is the 13th comparative example in lack of the visible light absorbing agent and the short-wavelength light absorbing agent. In the 13th comparative example, the contact lens is made of silicone hydrogel. A composition for manufacturing the silicone hydrogel of the 13th comparative example is listed in Table 51A.

TABLE 51A

| function | Ingredient | Content (wt %) |
| --- | --- | --- |
| monomer | 2-hydroxyethyl methacrylate | 4.8 |
| monomer | 3-methacryloyloxypropyltris (trimethylsilyloxy)silane | 26.00 |
| monomer | N-vinyl-2-pyrrolidinone | 19.50 |
| monomer | N,N-dimethyl acrylamide | 11.10 |
| monomer | methyl methacrylate | 4.10 |
| oligomer | polysiloxane macromer | 24.50 |
| initiator | 2-hydroxy-2-methyl-propiophenone | 1.00 |
| diluent | ethanol | 9.00 |

In the contact lens product according to the 13th comparative example, a visible light absorption rate of the contact lens is Avi, a blue light absorption rate of the contact lens is Abl, an ultraviolet light absorption rate of the contact lens is Auv, and the value of Avi, Abl and Auv of the 13th comparative example are listed in Table 51B.

TABLE 51B

13th comparative example

| Avi (%) | Abl (%) | Auv (%) |
| --- | --- | --- |
| 6.37 | 7.40 | 24.20 |

Figure 19:
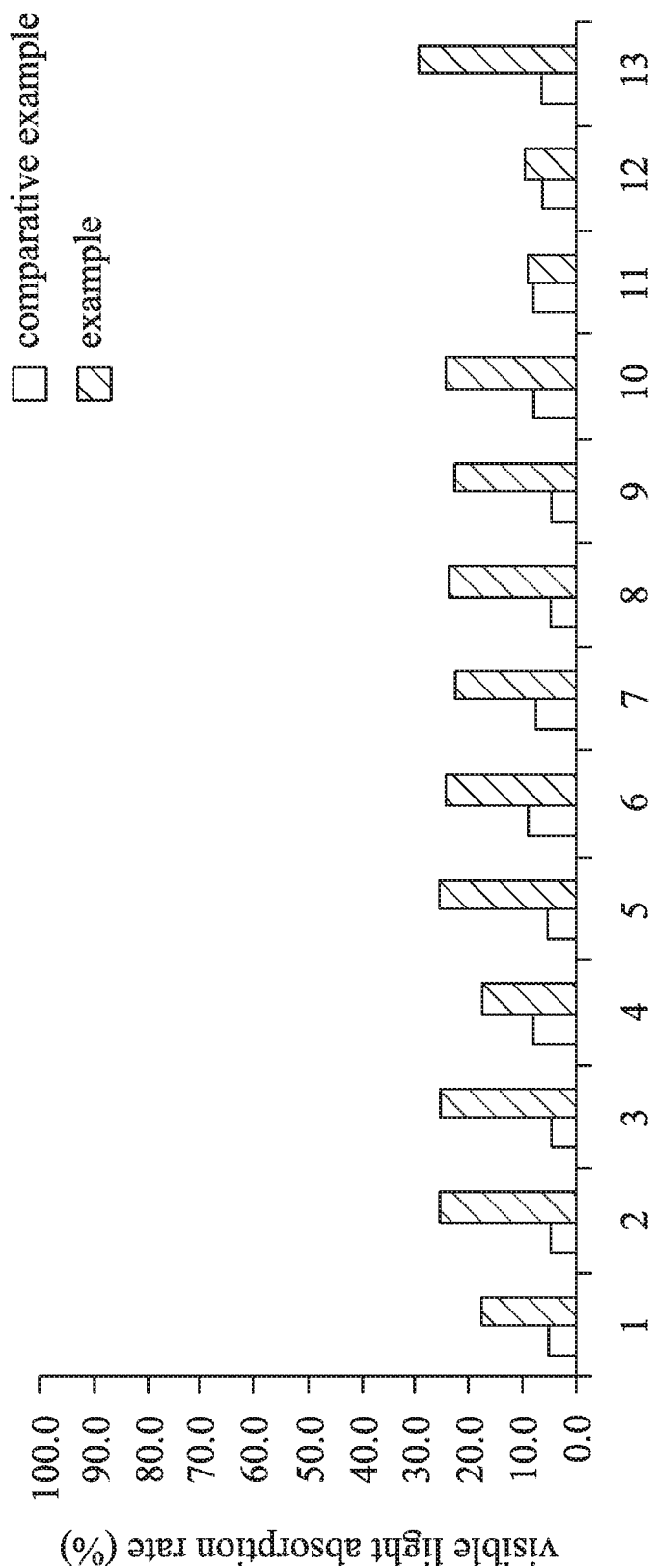
FIG. 19 shows visible light absorption rates of the contact lens of the 1st example to 13th example and visible light absorption rates of the contact lens of the 1st comparative example to 13th comparative example.

FIG. 19 shows the visible light absorption rates of the contact lens of the 1st example to 13th example and the visible light absorption rates of the contact lens of the 1st comparative example to 13th comparative example. As shown in FIG. 19, the visible light absorption rate of the contact lens of each of the 1st example to 13th example is higher than that of the correspondent comparative example thereof. It is obvious that the contact lens according to the present disclosure can ease the photophobia.

Figure 20:
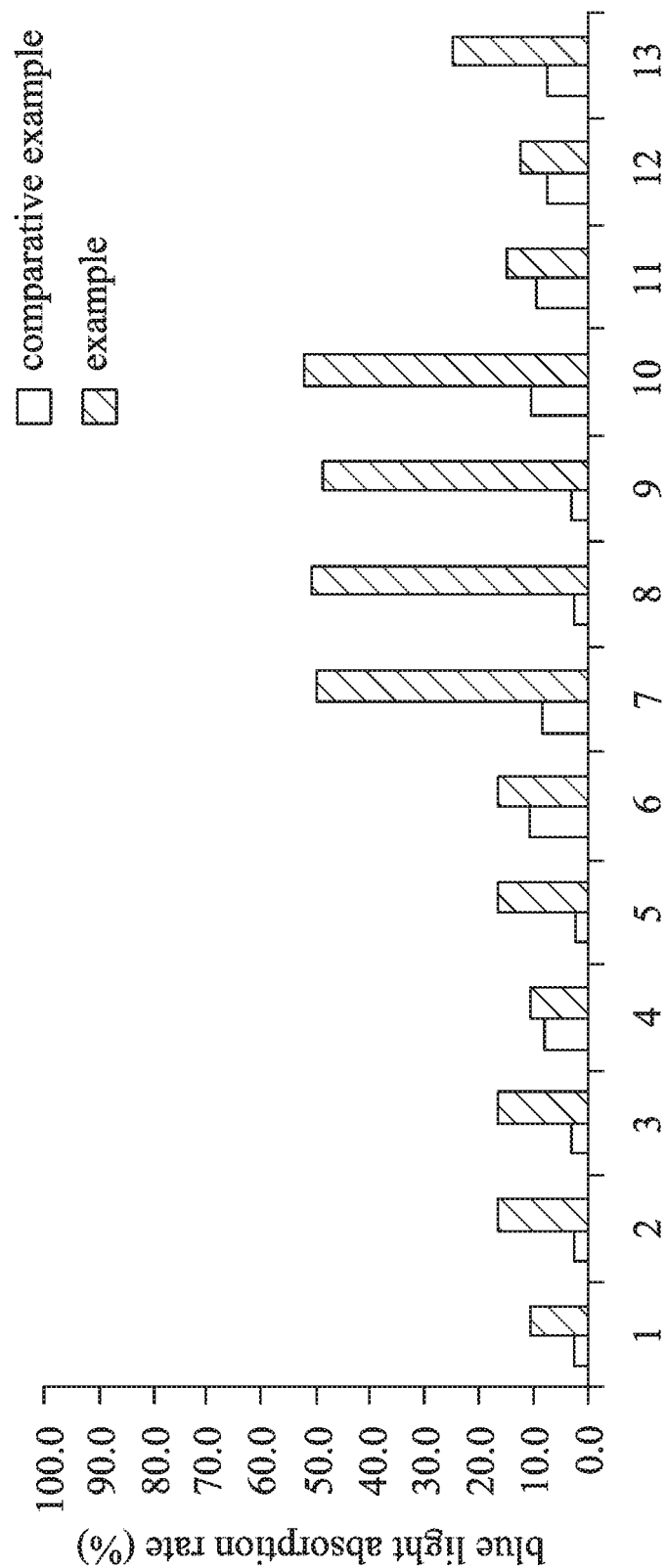
FIG. 20 shows blue light absorption rates of the contact lens of the 1st example to 13th example and blue light absorption rates of the contact lens of the 1st comparative example to 13th comparative example.

FIG. 20 shows the blue light absorption rates of the contact lens of the 1 st example to 13th example and the blue light absorption rates of the contact lens of the 1st comparative example to 13th comparative example. As shown in FIG. 20, the blue light absorption rate of the contact lens of each of the 1st example to 13th example is higher than that of the correspondent comparative example thereof. It is obvious that the contact lens according to the present disclosure can reduce the probability that the retina hurt by the blue lights.

Figure 21:
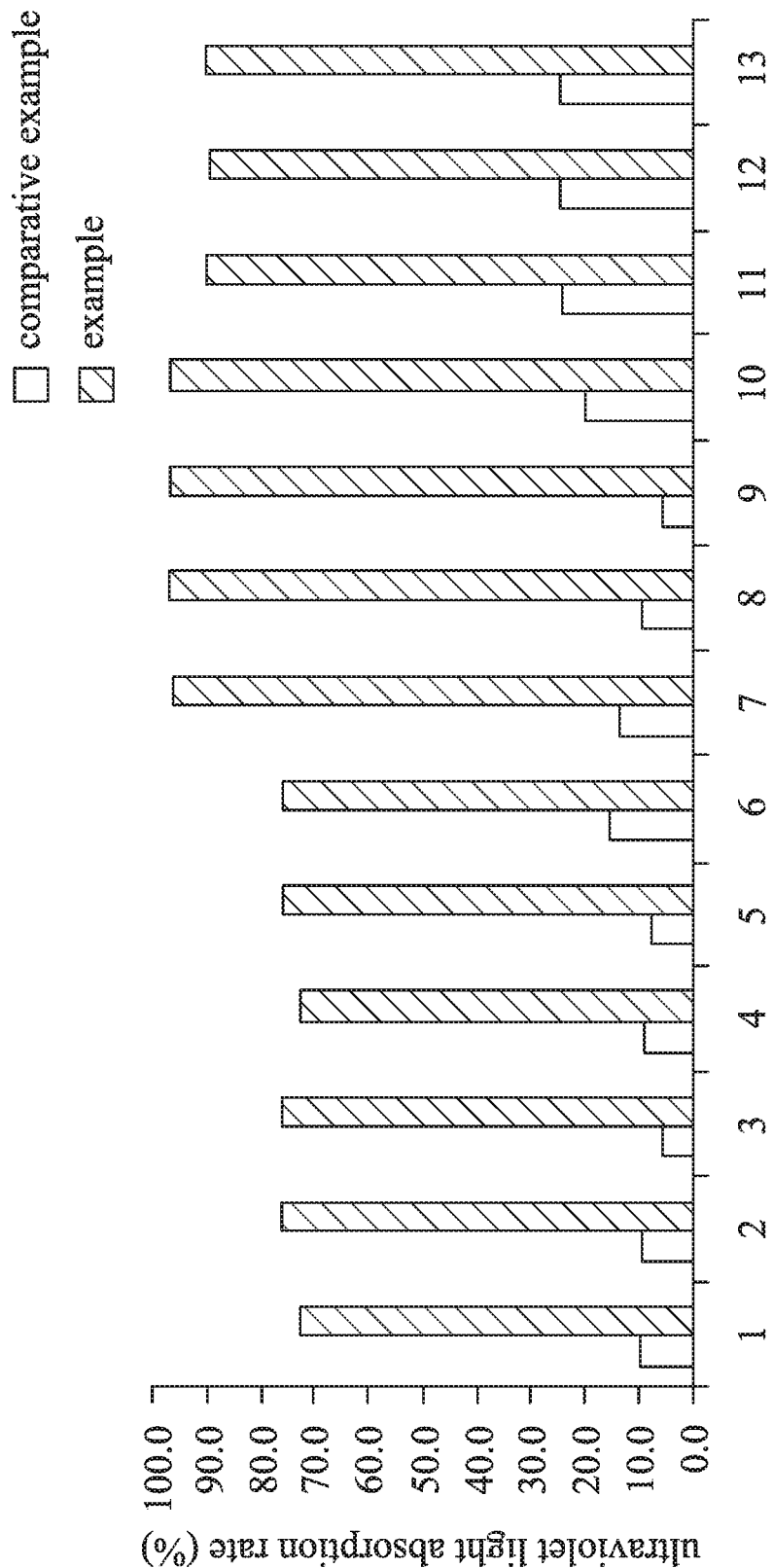
FIG. 21 shows ultraviolet light absorption rates of the contact lens of the 1st example to 13th example and ultraviolet light absorption rates of the contact lens of the 1st comparative example to 13th comparative example.

FIG. 21 shows the ultraviolet light absorption rates of the contact lens of the 1st example to 13th example and the ultraviolet light absorption rates of the contact lens of the 1st comparative example to 13th comparative example. As shown in FIG. 21, the ultraviolet light absorption rate of the contact lens of each of the 1st example to 13th example is higher than that of the correspondent comparative example thereof. It is obvious that the contact lens according to the present disclosure can reduce the probability that the retina hurt by the ultraviolet lights.

According to the contact lens of the present disclosure, an aspheric surface refers to a curved shape of a front surface or a back surface shown in a cross-sectional view taken along the central line of the contact lens. The front surface is a surface of the contact lens far away from the cornea, and the back surface is a surface of the contact lens close to the cornea.

According to the contact lens of the present disclosure, the diopter is represented by D. When the contact lens is for correcting myopia, the diopter thereof is negative; when the contact lens is for correcting hyperopia, the diopter thereof is positive.

According to the present disclosure, the cycloplegic agent can include but is not limited to atropine ((3-endo)-8-methyl-8-azabicyclo[3.2.1]oct-3-yl tropate), tropicamide (N-ethyl-3-hydroxy-2-phenyl-N-(4-pyridinylmethyl)propanamide), cyclopentolate (2-(dimethylamino)ethyl (1-hydroxycyclopentyl)(phenyl)acetate), homatropine ((3-endo)-8-methyl-8-azabicyclo[3.2.1]oct-3-yl hydroxy(phenyl)acetate), scopolamine ((1R,2R,4S,5S,7S)-9-methyl-3-oxa-9-azatricyclo[3.3.1.0$^{2,4}$]non-7-yl(2S)-3-hydroxy-2-phenylpropanoate), eucatropine (1,2,2,6-tetramethyl-4-piperidinyl hydroxy(phenyl)acetate) or the salt thereof. The cycloplegic agent, also known as a mydriatic agent, belongs to a parasympathetic blocker, i.e., a non-selective m-type muscarinic receptor blocker, which can control the paralysis and relaxation of the ciliary muscle of pupils by blocking the muscarinic receptor so as to enlarge the pupil.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A contact lens product, comprising:
   a contact lens; and
   a buffer solution, wherein the contact lens is immersed in the buffer solution, and the buffer solution comprises a cycloplegic agent;
   wherein a weight percentage concentration of the cycloplegic agent in the buffer solution is ConA, a visible light absorption rate of the contact lens is Avi, a blue light absorption rate of the contact lens is Abl, and the following conditions are satisfied:
   $0.01\% \leq ConA$;
   $0\% < Avi \leq 45\%$; and
   $10\% \leq Abl \leq 70\%$.

2. The contact lens product of claim 1, wherein the weight percentage concentration of the cycloplegic agent in the buffer solution is ConA, and the following condition is satisfied:
   $0.01\% \leq ConA < 0.5\%$.

3. The contact lens product of claim 1, wherein the visible light absorption rate of the contact lens is Avi, and the following condition is satisfied:
   $15\% \leq Avi \leq 25.5\%$.

4. The contact lens product of claim 3, wherein a composition for manufacturing the contact lens comprises at least one visible light absorbing agent, and the visible light absorbing agent is 1,4-bis[4-(2-methacryloxyethyl)phenylamino]anthraquinone or 1,4-bis[(2-methacryloxyethyl)amino]-9,10-anthraquinone.

5. The contact lens product of claim 1, wherein the contact lens is made of a silicone hydrogel.

6. The contact lens product of claim 5, wherein a composition for manufacturing the silicone hydrogel comprises at least two monomers, the monomer is 2-hydroxyethyl methacrylate, 3-methacryloyloxypropyltris(trimethylsilyloxy)silane, N-vinyl-2-pyrrolidinone, N,N-dimethyl acrylamide, methacrylic acid, methyl methacrylate, 3-(3-methacryloxy-2-hydroxypropoxy)propylbis(trimethylsiloxy)methylsilane or (3-acryloxy-2-hydroxypropoxypropyl) terminated polydimethylsiloxane.

7. The contact lens product of claim 1, wherein the contact lens is made of a hydrogel.

8. The contact lens product of claim 7, wherein a composition for manufacturing the hydrogel comprises at least two monomers, the monomer is 2-hydroxyethyl methacrylate, methacrylic acid, glycerol monomethacrylate or N-vinyl-2-pyrrolidinone.

9. The contact lens product of claim 1, wherein a composition for manufacturing the contact lens comprises at least one short-wavelength light absorbing agent, the blue light absorption rate of the contact lens is Abl, and the following condition is satisfied:
   $40\% \leq Abl \leq 60\%$.

10. The contact lens product of claim 9, wherein the short-wavelength light absorbing agent is 4-(phenyldiazenyl) phenyl methacrylate or reactive yellow 15.

11. The contact lens product of claim 10, wherein the ultraviolet light absorption rate of the contact lens is Auv, and the following condition is satisfied:
    $72.7\% \leq Auv \leq 96.8\%$.

12. The contact lens product of claim 11, wherein the short-wavelength light absorbing agent is 2-(2'-hydroxy-5'-methacryloxyethylphenyl)-2H-benzotriazole, 2-(4-benzoyl-3-hydroxyphenoxy)ethyl acrylate, 3-(3-(tert-butyl)-4-hydroxy-5-(5-methoxy-2H-benzo[d][1,2,3]triazol-2-yl)phenoxy) propyl methacrylate, 1,3-bis(4-benzoyl-3-hydroxyphenoxy)-2-propyl methacrylate, 1,3-bis(4-benzoyl-3-hydroxyphenoxy)-2-propanyl acrylate or N-(4-hydroxy-3-(5-methoxy-2H-benzo[d][1,2,3]triazol-2-yl)phenyl)methacrylamide.

13. The contact lens product of claim 1, wherein the contact lens comprises:
    a central region; and
    at least one annular region surrounding the central region, wherein a diopter of the annular region is different from a diopter of the central region, the annular region is a first annular region, the diopter of the central region of the contact lens is PowC, a maximum diopter of the first annular region of the contact lens is PowP1, and the following condition is satisfied:
    $2.25\ D \leq PowP1 - PowC$.

14. The contact lens product of claim 13, wherein the diopter of the central region of the contact lens is PowC, the maximum diopter of the first annular region of the contact lens is PowP1, and the following condition is satisfied:
    $2.25\ D \leq PowP1 - PowC \leq 12\ D$.

15. The contact lens product of claim 14, wherein a diameter of the central region of the contact lens is DiC, and the following condition is satisfied:
    $4\ mm \leq DiC \leq 8\ mm$.

16. The contact lens product of claim 15, wherein an outer diameter of the first annular region of the contact lens is DiP1, and the following condition is satisfied:
    $6\ mm \leq DiP1 \leq 16\ mm$.

17. The contact lens product of claim 16, wherein the diameter of the central region of the contact lens is DiC, the outer diameter of the first annular region of the contact lens is DiP1, and the following condition is satisfied:
    $0.27 \leq DiC/DiP1 \leq 0.64$.

* * * * *